United States Patent
Xavier Da Silveira et al.

(10) Patent No.: US 12,369,862 B2
(45) Date of Patent: *Jul. 29, 2025

(54) WEARABLE ATHLETIC MONITORING USING DIGITAL MODULATION

(71) Applicant: HAPPY HEALTH, INC., Austin, TX (US)

(72) Inventors: Paulo E. Xavier Da Silveira, Boulder, CO (US); David E. Clift-Reaves, Austin, TX (US); CJ Picklesimer, Washington, DC (US); Nithin O. Rajan, Austin, TX (US)

(73) Assignee: Happy Health, Inc., Austin, TX (US)

( * ) Notice: Subject to any disclaimer, the term of this patent is extended or adjusted under 35 U.S.C. 154(b) by 435 days.

This patent is subject to a terminal disclaimer.

(21) Appl. No.: 17/856,338

(22) Filed: Jul. 1, 2022

(65) Prior Publication Data

US 2022/0339789 A1    Oct. 27, 2022

Related U.S. Application Data

(63) Continuation of application No. 16/309,874, filed as application No. PCT/US2017/037343 on Jun. 13, 2017, now Pat. No. 11,375,958.

(Continued)

(51) Int. Cl.
*A61B 5/1455* (2006.01)
*A47L 11/24* (2006.01)
(Continued)

(52) U.S. Cl.
CPC ........... *A61B 5/7225* (2013.01); *A47L 11/24* (2013.01); *A61B 5/00* (2013.01); *A61B 5/0059* (2013.01);
(Continued)

(58) Field of Classification Search
None
See application file for complete search history.

(56) References Cited

U.S. PATENT DOCUMENTS 4,700,708 A    10/1987  New et al.
5,995,858 A    11/1999  Kinast
(Continued)

FOREIGN PATENT DOCUMENTS

WO    2017218598 A1    12/2017

OTHER PUBLICATIONS

International Preliminary Report on Patentability for International PCT Patent Application No. PCT/US2017/037343, mailed on Dec. 27, 2018, 4 pages.

(Continued)

*Primary Examiner* — Marjan Fardanesh
(74) *Attorney, Agent, or Firm* — Polsinelli PC

(57) ABSTRACT

System, method, and device is presented for generating and processing tissue-monitoring signals. An emitting driver is operable to control, upon receipt of at least one emitted signal, an optical emitter to emit at least one emitted signal. A processor is coupled to the at least one optical emitter and operable to execute instructions to generate the at least one emitted signal. At least one photodetector is operable to detect one or more photons transmitted through tissue and to convert the detected photons into a detected signal. A hardware processing sequence is coupled to the photodetector and processor. The hardware processing sequence is operable to filter and condition the detected signal. The processor is operable to execute instructions to demodulate the at least one emitted signal and the detected signal.

19 Claims, 33 Drawing Sheets

Related U.S. Application Data

(60) Provisional application No. 62/349,524, filed on Jun. 13, 2016.

(51) Int. Cl.
*A61B 5/00* (2006.01)
*B25J 9/16* (2006.01)
*B25J 11/00* (2006.01)
*B25J 13/00* (2006.01)
*G05D 1/00* (2006.01)
*A61B 5/01* (2006.01)
*A61B 5/11* (2006.01)

(52) U.S. Cl.
CPC .......... *A61B 5/0075* (2013.01); *A61B 5/1455* (2013.01); *A61B 5/14551* (2013.01); *A61B 5/6802* (2013.01); *A61B 5/7228* (2013.01); *A61B 5/7246* (2013.01); *B25J 9/1664* (2013.01); *B25J 9/1682* (2013.01); *B25J 11/0085* (2013.01); *B25J 13/006* (2013.01); *G05D 1/0027* (2013.01); *G05D 1/0236* (2013.01); *A61B 5/0002* (2013.01); *A61B 5/01* (2013.01); *A61B 5/1112* (2013.01); *A61B 2562/0238* (2013.01)

(56) References Cited

U.S. PATENT DOCUMENTS

| | | |
|---|---|---|
| 7,356,364 B1 | 4/2008 | Bullock et al. |
| 2010/0217098 A1 | 8/2010 | LeBoeuf et al. |
| 2012/0217098 A1 | 8/2012 | Putkinen et al. |
| 2012/0253153 A1 | 10/2012 | Trumble |
| 2012/0303081 A1 | 11/2012 | Donofrio |
| 2012/0310060 A1 | 12/2012 | Baker et al. |
| 2015/0230743 A1 | 8/2015 | Silveira et al. |

OTHER PUBLICATIONS

International Search Report and Written Opinion for corresponding PCT Application No. PCT/US2017/037343, mailed on Aug. 31, 2017, 5 pages.

WEARABLE ATHLETIC MONITORING USING DIGITAL MODULATION

CROSS REFERENCE TO RELATED APPLICATION

This application is a continuation application of U.S. patent application Ser. No. 16/309,874, filed Dec. 13, 2018, which is a U.S. National Stage Entry of PCT Application No. PCT/US2017/037343, filed Jun. 13, 2017, which claims priority to U.S. Provisional Application No. 62/349,524 filed Jun. 13, 2016, the entire contents of each are incorporated by reference.

FIELD

The present disclosure generally relates to a method and device for non-invasive tissue monitoring using near-infrared light. Additionally, the disclosure relates to a device, system, and method for differentiation of light emitted by the device from background illumination using digital modulation.

BACKGROUND

Wearable tissue monitoring is increasingly popular, particularly—but not exclusively—among athletes. There are several different types of devices that athletes are purchasing to increase their performance. One device is the chest strap that measures heart rate. Additionally, there are several devices that are designed to be worn on the wrist. Some of these devices simply track motion through steps or through the Global Positioning System (GPS). These devices can also include information such as time or convey other messages such as receipt of email to the user.

BRIEF DESCRIPTION OF THE DRAWINGS

So that the manner in which the above recited features of the present disclosure can be understood in detail, a more particular description of the present disclosure, may be had by reference to examples, some of which are illustrated in the appended drawings. It is to be noted, however, that the appended drawings illustrate only typical example, and are therefore not to be considered limiting of its scope, for the disclosure may admit to other equally effective examples.

DETAILED DESCRIPTION

Figure 1:
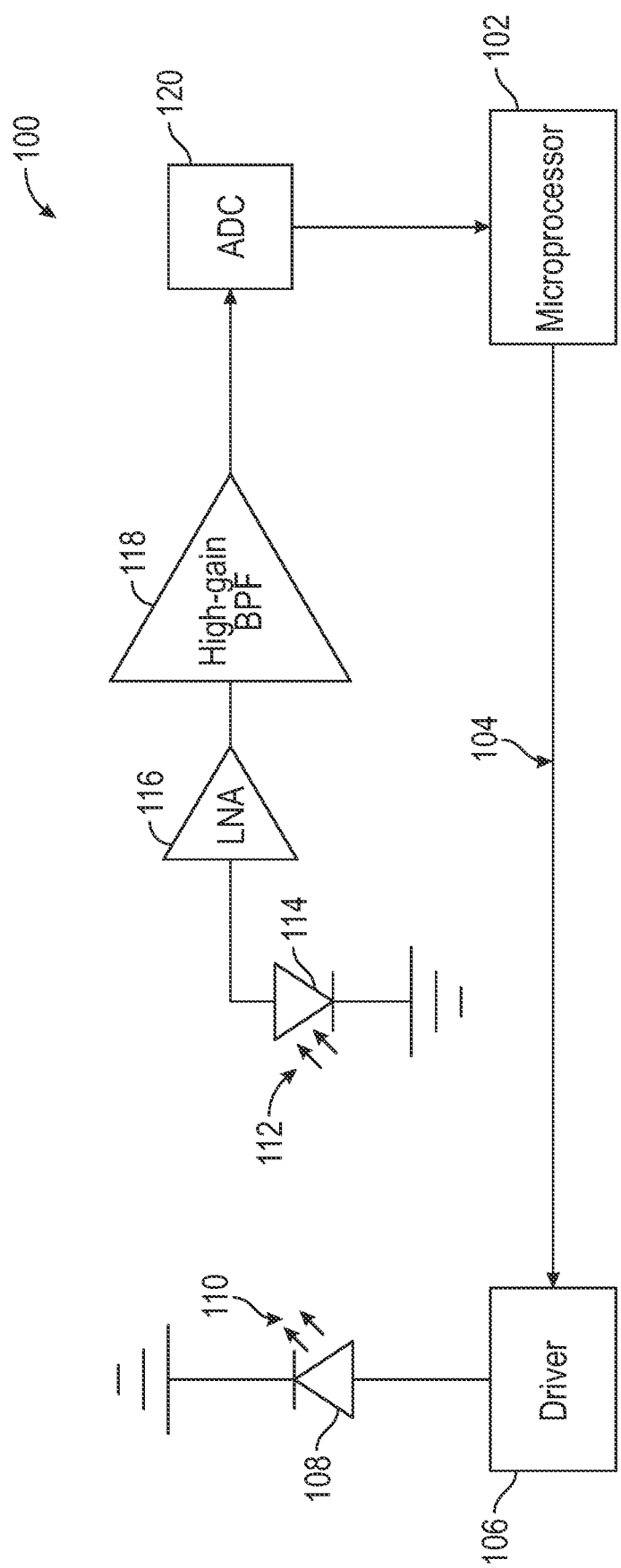
FIG. 1 is a schematic diagram of a digital optical tissue monitoring system robust to ambient light, according to an example of this disclosure.

Various examples of the disclosure are discussed in detail below. While specific implementations are discussed, it should be understood that this is done for illustration purposes only. A person skilled in the relevant art will understand that other components and configurations can be used without departing from the spirit and scope of the disclosure.

It should be understood at the outset that although illustrative implementations of one or more examples are illustrated below, the disclosed device can be implemented using any number of techniques. The disclosure should in no way be limited to the illustrative implementations, drawings, and techniques illustrated herein, but can be modified within the scope of the appended claims along with their full scope of equivalents.

Unless otherwise specified, any use of any form of the terms "connect," "engage," "couple," "attach," or any other term describing an interaction between elements is not meant to limit the interaction to direct interaction between the elements and can also include indirect interaction between the elements described. In the following discussion and in the claims, the terms "including" and "comprising" are used in an open-ended fashion, and thus should be interpreted to mean "including, but not limited to . . . ". The various characteristics described in more detail below, will be readily apparent to those skilled in the art with the aid of this disclosure upon reading the following detailed description, and by referring to the accompanying drawings.

Note that the term tissue, as used in this application, may denote not only human tissue but also animal, fruit, vegetable, and plant tissue. For example, the disclosed subject matter may be used to determine the level of carotene in a vegetable, or the tissue oxygenation in an animal.

The present disclosure generally relates to a system for generating and processing tissue-monitoring signals. The system includes several components, including: a microprocessor capable of generating at least one signal, a light emitter driver connected to the microprocessor, at least one light emitter operable to emit light towards a tissue, at least one photodetector operable to detect light after propagation through the tissue, and at least one processing sequence operable to process the analog signal detected by the photodetector and conditioning it for analog-to-digital conversion. A processing sequence as described herein includes one or more hardware components. For example, the processing sequence can include at least one of an amplifier, a band-pass filer or an analog-to-digital converter (ADC). The amplifiers can be operational amplifiers, for example, high noise amplifiers, high gain amplifiers, low noise amplifiers, or any other suitable amplifier. The present disclosure generally concerns light emitters and associated detectors. In at least one example, the light emitters can be light emitting diodes (LEDs). In other examples, the light emitters can include a lower-powered laser, quasi-monochromatic light source, LED, or lasers, such as solid-state lasers or vertical cavity emitting lasers (VCSELs), or any combination thereof. While specific examples presented herein are described in relation to LEDs, other light emitters are considered within the scope of the present disclosure and can be inserted into the relevant portion of the description.

The light emitting diode driver, upon receipt of at least one emitted signal directs the optical emitters, which in one example can be LEDs, to emit the emitted signal into a tissue. The emitted signal is reflected and absorbed by the tissue, and a photodetector in the system can detect any photons transmitted through and/or from the tissue. The photodetector then converts the detected photons into a detected signal, so that a processing sequence connected to the photodetector can filter and condition the detected signal. The processing sequence is connected to and performed by the microprocessor, and the microprocessor then demodulates the emitted signal and the detected signal.

The orthogonal signal generated by the microprocessor can be a linear chirp repeatedly multiplied by the columns of a Hadamard matrix. The order of the Hadamard matrix needs to be equal to or greater than the number of light emitting diodes. In an alternative example, the orthogonal signal generated by the microprocessor can be a maximal length pseudorandom number sequence, making the signal automatically broadband and its segments automatically orthogonal to each other.

Wearable athletic monitoring requires the use of non-invasive devices that are able to overcome motion and intense ambient light, namely, sunlight. Near-infrared light in the range from 650 nanometers to 1100 nanometers presents the combined advantage of penetrating deep into biological tissue while being effectively detected by low-cost Silicon photodiodes. However, the same light transparency that makes near-infrared light attractive for monitoring tissue deeply also makes near-infrared devices vulnerable to ambient light. This disclosure describes a system using digital modulation to differentiate the light emitted by the device from background illumination.

The present system is operable to provide enhanced performance in ambient light conditions. Examples of the improvements are, but are not limited to, increased accuracy, which can include a reduced numeric error in the tissue monitoring, and increased robustness, which can include increased tolerance to a wider range of use conditions. The present disclosure can be implemented in relation to a wide variety of different form factors and/or configurations. In at least one form factor, the present technology is designed to fit on a wrist or forearm. In other form factors, the present technology can be implemented to be on the upper arm, lower leg, upper leg, or on the torso, around the ankle of the user, or any other suitable area of the body. In still other examples, the technology can be used in multiple areas for measuring different tissues so that it can be implemented in a configuration that places it near or in contact with the tissue in question.

FIG. 1 depicts a digital optical tissue monitoring system 100 robust to ambient light, according to an example of this disclosure. A processor 102, is used to generate at least one emitted signal 104, which, in at least one example, can be orthogonal to each other in the case when the at least one signal is at least two signals. In at least one example, the processor 102 can be a microprocessor. Each of the signals is input into an optical emitter driver 106 which outputs signals to drive a corresponding emitting device, such that the emitting device 108 emits an optical signal 110. A portion or fraction of the optical signal 110 from the optical emitting device can be detected by a photodetector (PD) 114. The portion or fraction of the optical signal can be represented as 112, which is also described as detected photons. The photodetector can have an optical responsivity which varies with the wavelength of the at least one optical emitting device. The responsivity of the photodetector 114 can convert detected photons 112 into a photocurrent. As tissue can present dispersion, the modulation of the optical signal can be reduced. The photocurrent is then amplified and converted into a voltage signal using a transimpedance amplifier (TIA). The TIA can be implemented by a single or multiple stages of amplifiers. In one example, there are two stages in which the first stage provides low-noise and low-gain amplification using a Low-Noise Amplifier (LNA) 116 followed by a second stage with a high-gain amplifier including a band-pass filter (BPF) 118 with an amplification frequency spectrum matching that of the broadband signal of interest. This way SNR is improved by boosting the signal with the LNA 116 while blocking out-of-band noise using the BPF 118. The signal is then digitized by the ADC 120.

In one example, the microprocessor 102 can generate each one of the N orthogonal emitted signals $c_i(t)$, where i is an index ranging from 1 to N. Each signal drives one of the N LEDs, thus modulating their optical power from $P_0$ into $P_0 c_i(t)$. The optical signal is detected by a photodetector with an optical responsivity that varies with the wavelength $\lambda$ of the LEDs. This responsivity $R(\lambda)$ converts detected photons into a photocurrent i(t). Tissue also presents dispersion, resulting in a reduction in the modulation of the optical signal given by $M(\rho,\mu_a,\mu_s',\lambda)$. This effect, combined with the photodetector capacitance, are two factors that create an upper bound to the maximum frequency over which the spread-spectrum signal can be modulated, hence also creating an upper bound on the achievable processing gain. For simplicity of notation, the effect of dispersion on the optical signal amplitude, when relevant, can be assumed to be already included in the term $R(\rho,\mu_a,\mu_s',\lambda)$.

Spread-spectrum modulation can include using broadband signals to modulate emitted light. Since interfering light is not modulated the same way, demodulation makes it possible to decode the detected light signal in order to separate the light emitted by the device from light emitted by other sources. The demodulation can be performed, for example, by using a cross-correlation between the original signal and the detected signal. Information about the optical transmission of tissue at a given wavelength can be used, for example, in spectroscopy to determine tissue properties such as oxygenation state, hydration state, total hemoglobin, lipid concentration, cytochrome oxidase concentration, melanin concentration, beta-keratin concentration, lactate concentration, chlorophyll concentration, myoglobin concentration, and concentration of different chromophores, is given by the amplitude of the correlation peak.

Processing gain is the amount of signal gain over uncorrelated background noise achieved during cross-correlation, and the processing gain is directly proportional to the temporal-bandwidth product of the underlying signal. That is, the higher the range of frequencies and the larger the duration of the signal, the larger the resulting increase in signal-to-noise ratio (SNR). Optical simulations have shown that for a wrist based application, in which very limited light-blocking is available, processing gains of at least 20 dB are needed. This can be achieved, for example, by employing a spread-spectrum signal with a 500 Hz bandwidth in 0.2 s (5 Hz repetition rate). These simulations were later confirmed by experimental implementations.

When the emitted signals are orthogonal, multiple signals can be encoded/decoded simultaneously. Code-division multiplexing alleviates the requirements of time multiplexing. For example, when modulating N number of optical emitters, all of the emitters may be illuminated simultaneously, thus removing the requirement of dividing each time slot into N slots. On the other hand, code-division multiplexing increases the bandwidth requirements by the same amount (N), resulting in no net increase in processing gain.

Figure 2:
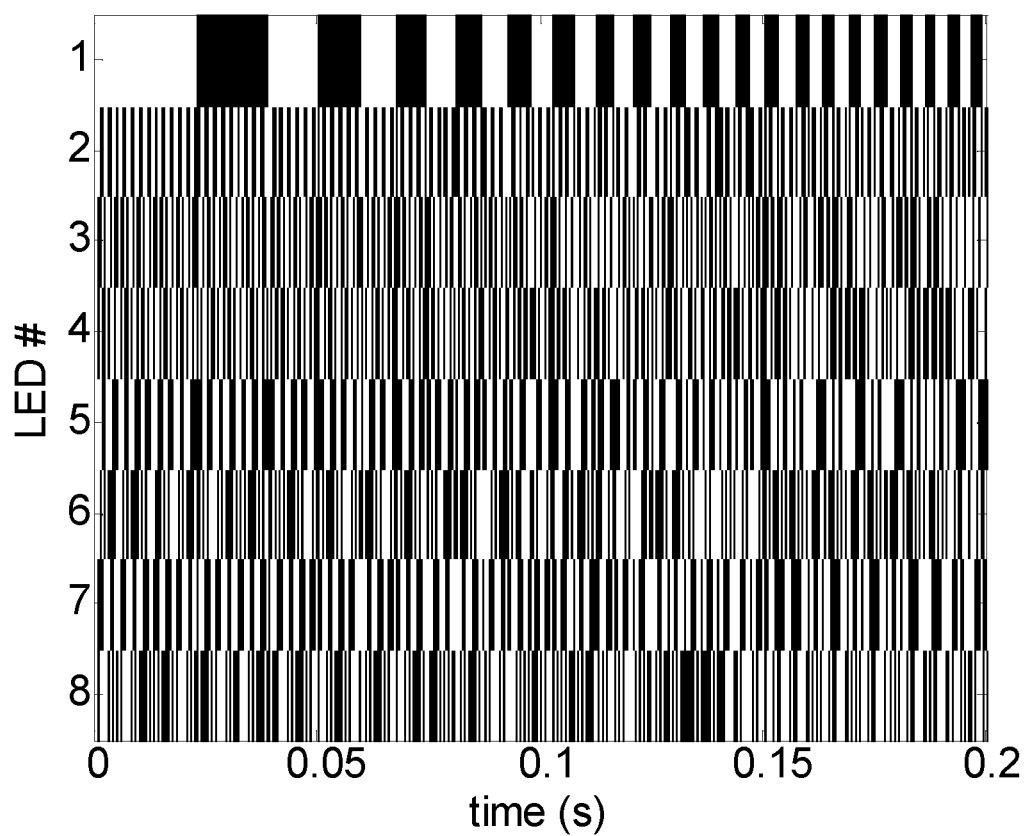
FIG. 2 is an example of a broadband chirp signals orthogonalized using an order-8 Hadamard matrix.

FIG. 2 shows an example of a linear chirp repeatedly multiplied by an order-8 Hadamard matrix, resulting in the orthogonal codes necessary to encode a system with 8 LEDs over time. The original chirp (before 1-bit digitization) is given by $c(t)=\cos(\pi t^2 r)$, where r is the chirp rate. Such a signal has a time-varying frequency given by $f(t)=t.r$. In the example below r=1 kilohertz per second (kHz/s), t ranges from zero to 0.2 s, resulting in $\Delta f=200$ Hz and a temporal-bandwidth product of 40.

Figure 3:
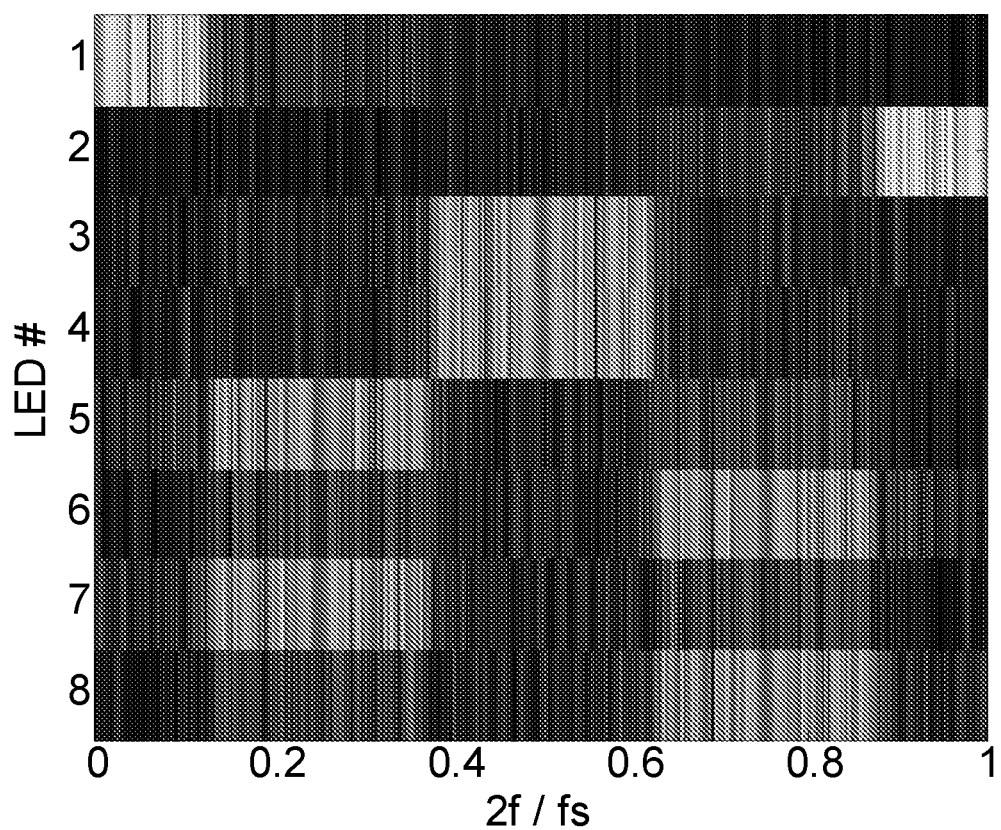
FIG. 3 is an example depiction of the frequency spectrum of the Hadamard-transformed signals of FIG. 2.

Multiplication by the Hadamard matrix resulted in an N-fold increase in the maximum signal frequency, as illustrated in FIG. 3, which shows the Fourier transform of the same signals shown in FIG. 2. The top row (optical emitter 1, here depicted as LED 1, with the original digitized chirp) has a bandwidth limited to one-eighth (⅛) of the Nyquist frequency (½ fs where fs is the sampling frequency). Note that some signal power is present beyond one-eighth of the Nyquist frequency and that is the result of digitization, equivalent to convolving the original chirp spectrum with a sinc function, the Fourier transform of a square wave. The signal immediately below it (optical emitter 2, here depicted as LED 2) has highest frequency components going all the way to the Nyquist frequency, which is eight (8) times larger than the larger frequency of interest of the original chirp.

Digitizing broadband linear chirps is one example of a method used to generate a broadband (i.e., spread-spectrum) signal with a high spatial-temporal bandwidth product. Another technique capable of efficiently creating broadband signals in a processor (which may include a microprocessor or a micro-controller, for example) is using the mathematical technique of generating pseudorandom binary sequences. Such sequences can be efficiently generated in a microprocessor using shift registers and exclusive-OR (XOR) operations. In particular maximal length sequences of pseudorandom numbers are particularly useful given their ability to generate long, broadband and orthogonal binary sequences with minimum hardware requirements. For example, using the so-called $PRBS15=x^{15}+x^{14}+1$, a sequence of 15-bit binary numbers can be generated that only repeats itself once every $2^{15}-1=32,767$ times using only a 15-bit shift register and a 3-input XOR gate.

Figure 4:
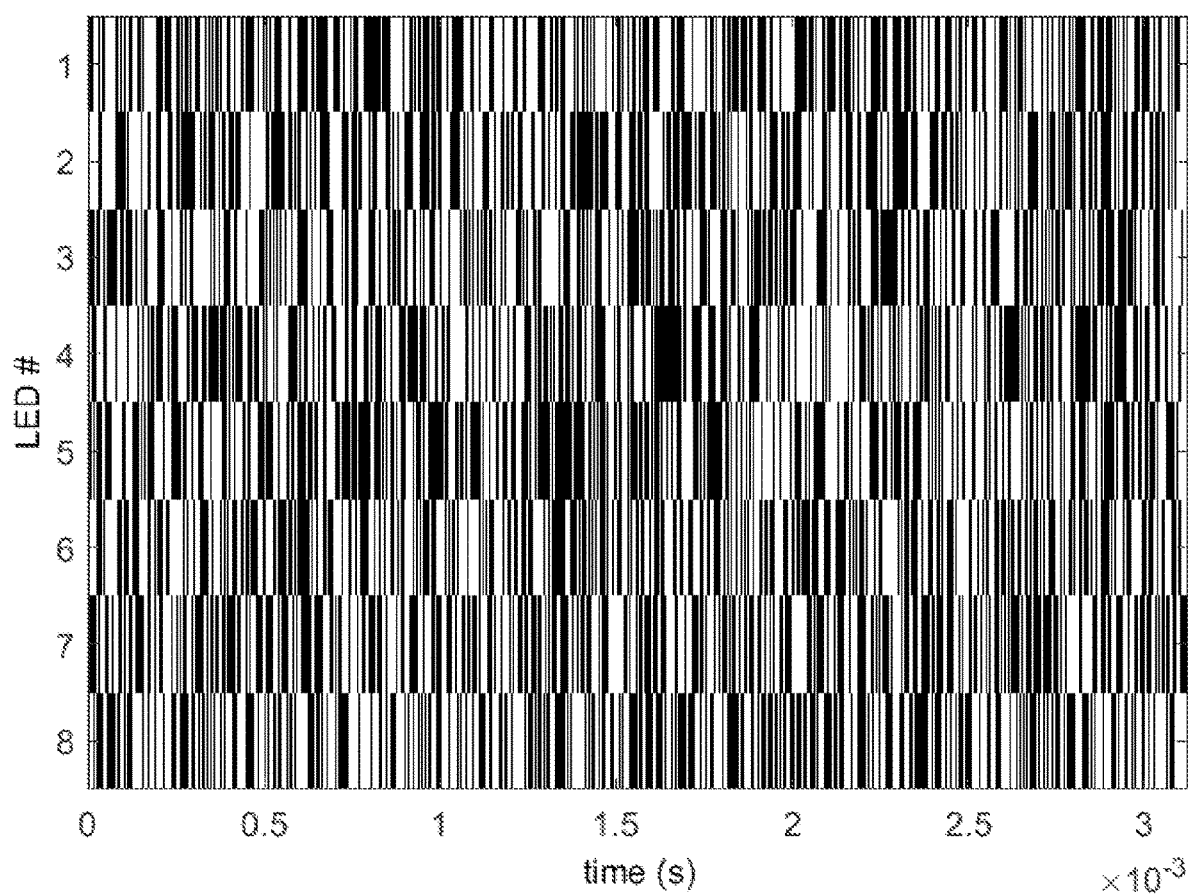
FIG. 4 is an example depiction of a spread-spectrum pseudorandom number signal.

FIG. 4 shows an example of an eight-channel signal obtained from a long pseudorandom sequence, such as that provided in FIG. 3. The sequence is long enough that it is possible to generate values for all 8 channels without needing to use a multiplication with a Hadamard matrix. That is, the pseudorandom number generator is operable to generate with a sequence that is orthogonal with respect to its own segments, up to the maximum sequence length.

Figure 5:
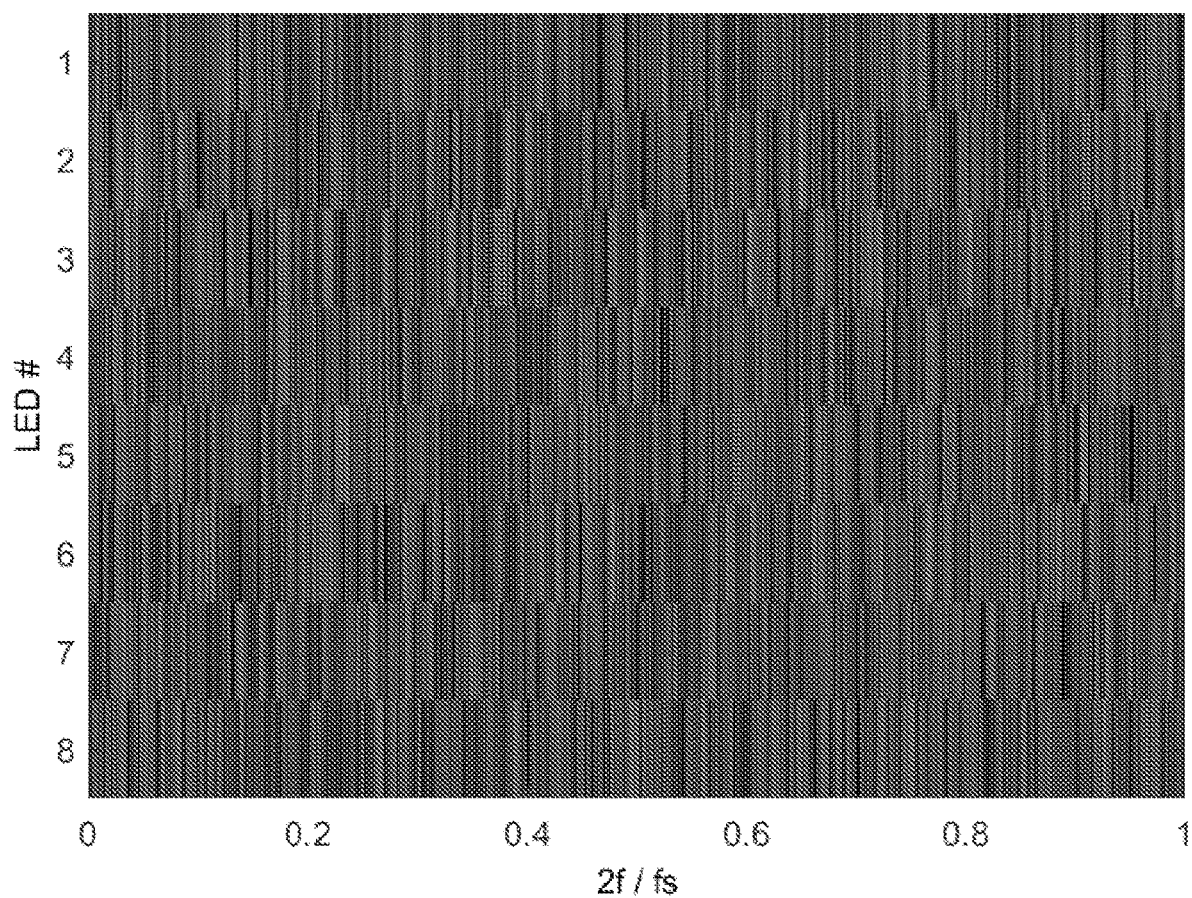
FIG. 5 is an example depiction of the frequency spectrum of the pseudorandom number sequence from FIG. 4.

The broadband nature of the sequence is demonstrated by a magnitude of a Fourier Transform, such as that plotted in FIG. 5. In the example shown in FIG. 5, the sampling rate is set to 96 k Samples/s and the sequence length to 4096 samples, resulting in a sampling period of about 21.328125 milliseconds (ms). FIG. 5 further demonstrates that all of the channels are broadband. For clarity, FIG. 4 only shows the first 3 milliseconds (ms) of the sequence.

Figure 6:
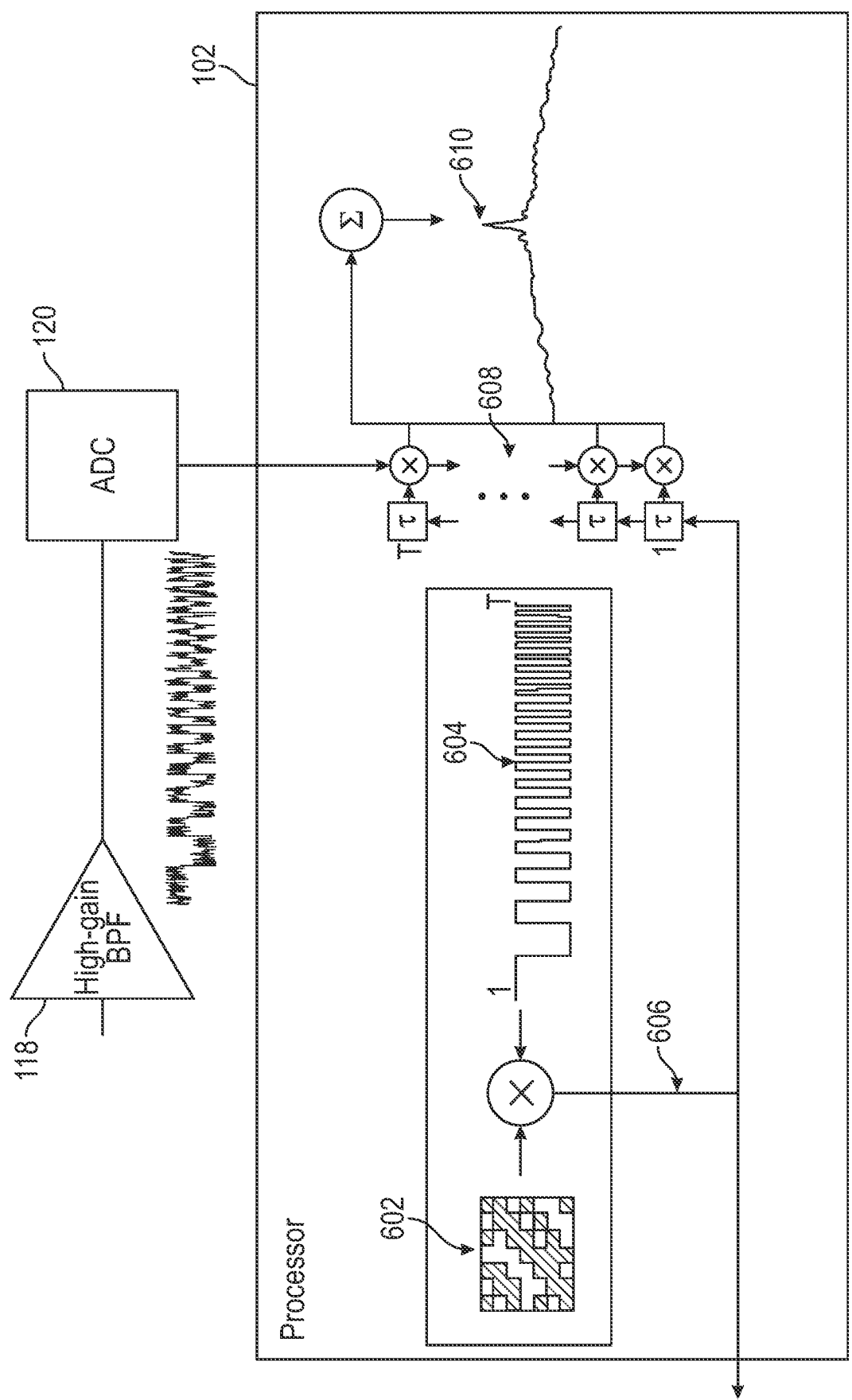
FIG. 6 is an example schematic diagram of the digital signal processing performed by a microprocessor according to this disclosure, using a linear chirp orthogonalized with a Hadamard matrix signal.

The diagram in FIG. 6 shows the digital signal processing performed by the processor 102 using a linear chirp 604 as an example of a broadband spread-spectrum signal. The N broadband orthogonal codes $c_i(t)$ (wherein i ranges from 1 to N) are generated by sequentially multiplying the original linear chirp c(t) by the rows (or columns) of an order-N Hadamard matrix 602 (an order-8 Hadamard matrix is shown in this example). The same N codes are used to demodulate the detected signals and separate the signals originated by each optical emitter. Light emitted by each emitter, after propagation through tissue, is detected by photodiode 114 (FIG. 1) generating a photocurrent that is first amplified by the LNA 116 (FIG. 1) and then by the high-gain amplifier and filtered by the BPF 118, and then digitized by the ADC 120. Correlation is performed, for example, using a tapped-delay line 608, wherein delayed versions of the orthogonal emitted signals 606 are multiplied by the ADC output and summed, resulting in a cross-correlation between signals 606 and the ADC output. After cross-correlation, a correlation peak is given by $p(k)=KR(t)\Sigma(c_k)^2$ where K is a proportionality constant that is best determined through calibration [the term $\Sigma(c_k)^2$ is shown for clarity but is also a constant term that is taken into account during calibration]. Therefore, the term $\Sigma(c_k)^2$ can simply be written as a constant for certain conditions. Also for clarity, the term R(t) is shown as a function of time only, since we are usually interested in monitoring the temporal variations of $\mu_a$ and $\mu_s'$. Note that the multiplication with the Hadamard matrix is not needed when N=1, or when using a pseudo-random sequence generator.

Figure 7:
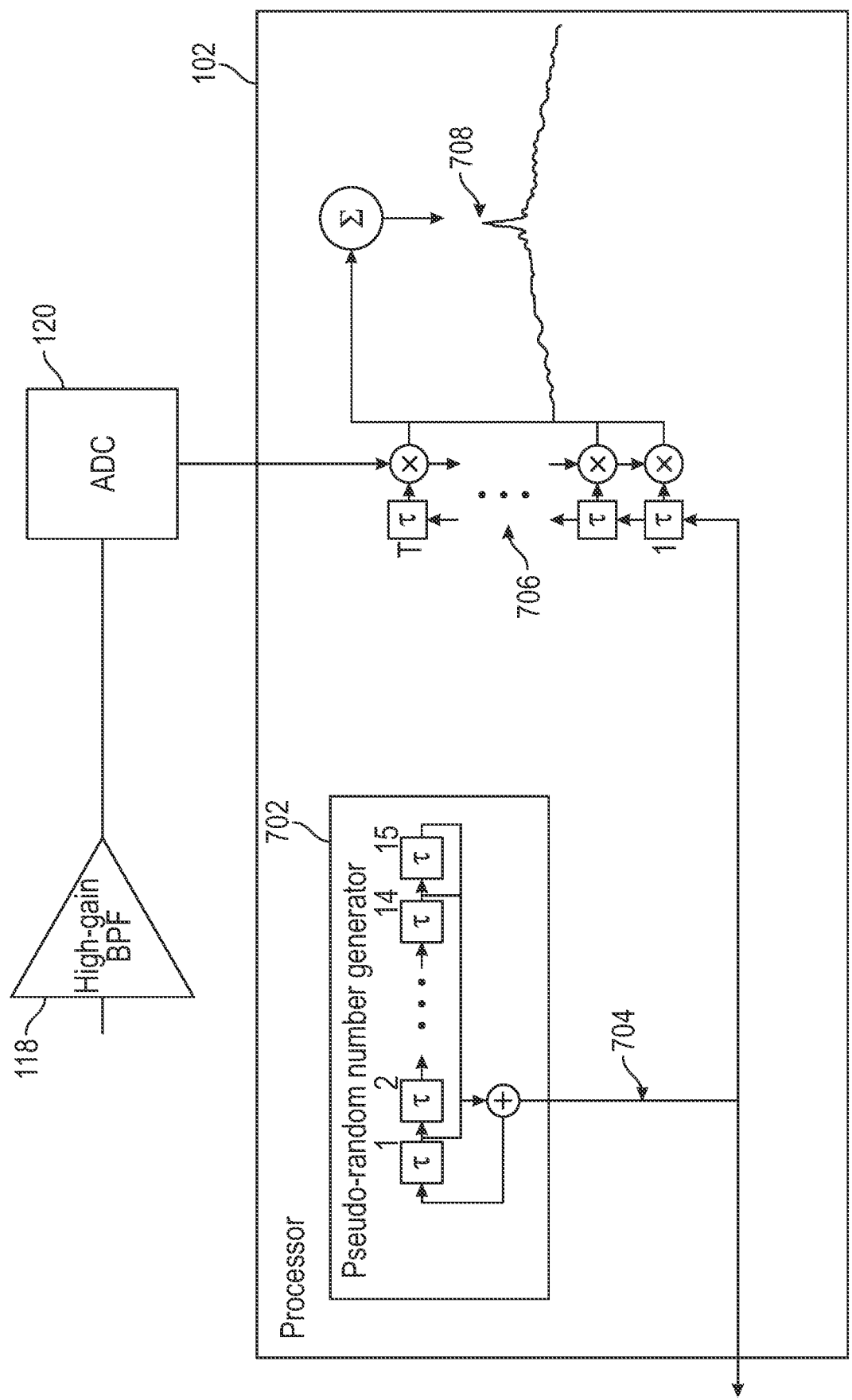
FIG. 7 is an example schematic diagram of the digital signal processing performed by a microprocessor according to this disclosure, using a pseudorandom number sequence signal.

The diagram in FIG. 7 shows the digital signal processing performed by the processor 102 in the case when the signal is generated using a pseudorandom sequence. The symbol, +, denotes an XOR operation, τ denotes one time-step of delay, x denotes multiplication and Σ denotes summation. Light emitted by each optical emitter, after propagation through tissue, is detected by photodiode 114 (FIG. 1) generating a photocurrent that is first amplified by the LNA 116 (FIG. 1) and then by the high-gain amplifier and filtered by the BPF 118, and then digitized by the ADC 120. Correlation is performed using a tapped-delay line 706, wherein delayed versions of the orthogonal signal 704 are multiplied by the ADC output and summed, resulting in a cross-correlation between signals 704 and the ADC output. In this example, the broadband orthogonal signal 704 is generated using the pseudorandom number generator 702 to produce a PRBS15 maximum length sequence as the emitted signal (other maximum length sequences could be used, for example, PRBS7, PRBS16 and PRBS19). The pseudorandom number generator is implemented by a linear shift register combined with a three-input XOR gate, and the cross-correlation between the pseudorandom number sequence and the detected signals is implemented by a linear shift register in which each shifted pseudorandom sequence element is summed with its multiplication by the input signal detected at step k, resulting in a cross-correlation signal with a peak 708. Each one of the N peak signals 708 is produced by cross-correlation with each one of the N modulating signals 704 used to drive each one of the N optical emitters, and each peak 708 is proportional to the signal R(t) monitored by each optical emitter at its corresponding spatial location ρ and wavelength λ.

It should be noted that a single shift register can be shared for both operations (pseudorandom number generation and cross-correlation), making this implementation especially suitable for embedded implementation in a microprocessor, a micro-controller, or even using discrete components.

Figure 8:
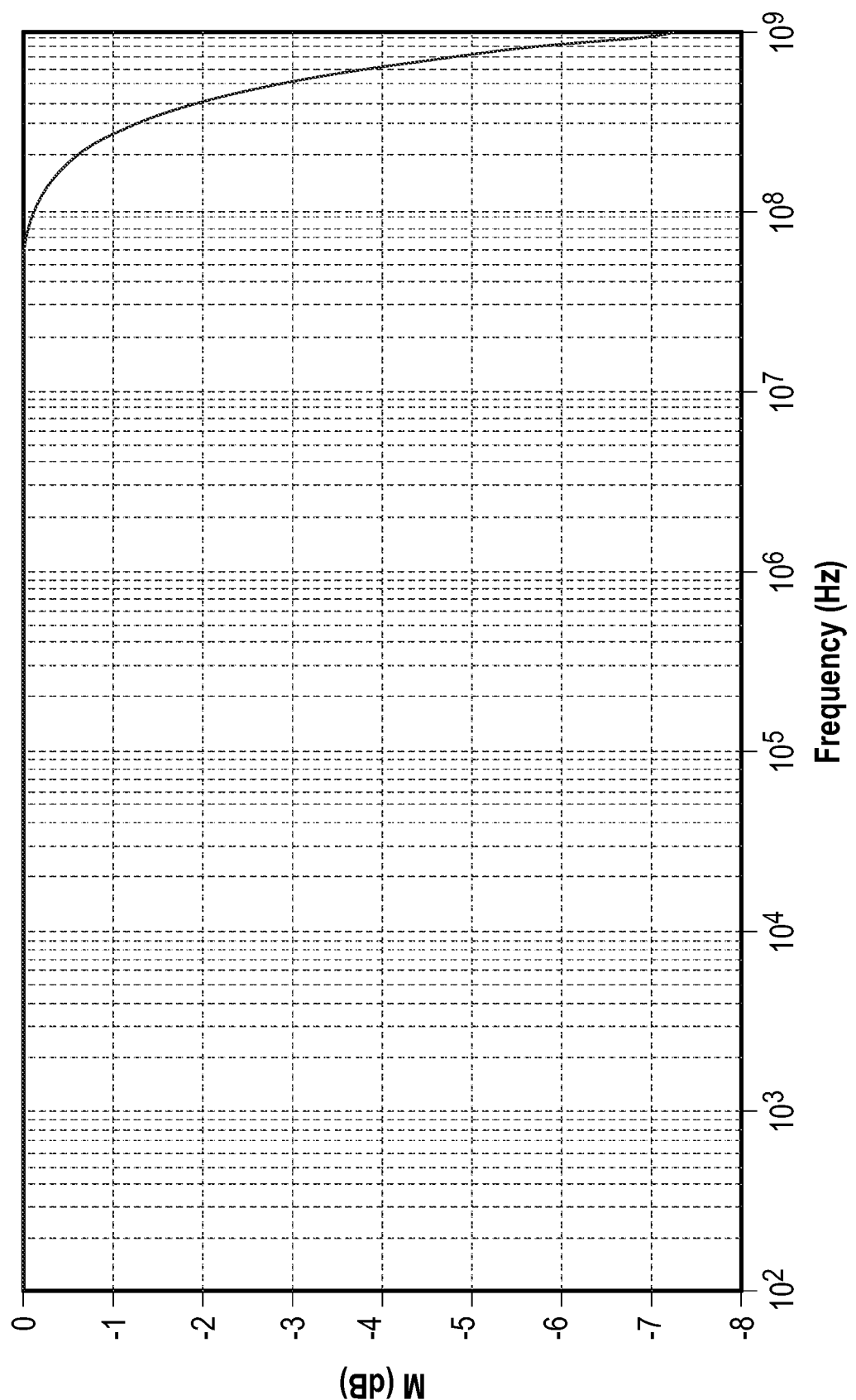
FIG. 8 is an example plot of the Modulation Index M as a function of modulating frequency.

FIG. 8 shows a plot of a modulation index as a function of modulating frequency. As shown in FIG. 8, a plot of the modulation index M is at an emitter/detector separation distance ρ=27 mm in a typical piece of tissue (absorption coefficient, $\mu_a$=0.01/mm, reduced scattering coefficient, $\mu_s'$=1.25/mm, index of refraction=1.378 at λ=700 nm) as a function of modulating frequency, showing that M is close to unity until the frequency approaches 100 MHz. Given the sampling frequencies in consideration (192 kSamples/s) and the highest cutoff frequency of the band pass filter (200 kHz), M can be unity and can be safely ignored. FIG. 8 demonstrates that tissue dispersion has a negligible effect on modulation until a frequency of about 100 MHz. While the example(s) use ρ=27 mm, other examples can include ρ=7.3 mm, ρ=12.5 mm, or ρ=17.7 mm. Still in other examples, ρ>5 mm and ρ<50 mm.

Most of the photons injected by light emitting diodes into tissue may not make it to the photodetector. Many are absorbed by tissue and many more are scattered away. This is reflected by the factor R(ρ,$\mu_a$,$\mu_s'$,λ), which is in fact the signal of interest. The photocurrent detected by the photodetector is given by:

$$i(t)=P_0 R(\rho,\mu_a,\mu_s',\lambda,t) \mathcal{R}(\lambda)[c_i(t)+n(t)]$$

where n(t) represents a lump sum of all noise sources, modeled as Gaussian additive white noise, and where the functional dependence of R on time (t) comes from the temporal variation of the tissue properties, $\mu_a(t)$ and $\mu_s'(t)$. The temporal relationship of the tissue properties results in a temporal variation of R and, hence, i(t).

Following photodetection the signal can be filtered and conditioned for digitization. A low-noise amplifier can be used for conditioning of the signal. A high-gain amplifier and a bandpass filter can be used to further filter and condition the signal. For example, a high-gain amplifier and bandpass filter centered at the center frequency of the signals $c_i(t)$ and with a bandwidth matching that of those signals can be used to further filter and condition the signal. In at least one example, the high-gain bandpass filter bandwidth is NΔf centered at NΔf/2 (or higher). Bandpass filtering effectively cuts off a large portion of DC ambient light, but the large bandwidth required by the spread-spectrum signals results in a large fraction of noise power passing through the band pass filter. The remaining noise will be removed by the digital processing gain performed in the microprocessor. In one example, the signal output of the BPF can be represented by $$s_i(t)=GP_0 R(\rho,\mu_a,\mu_s',\lambda,t) \mathcal{R}(\lambda) \int h(t-t')[c_i(t')+n(t')]dt'$$

where G is the combined gain of all amplifiers (usually dominated by the gain of the last-stage, high-gain amplifier) and h(t) is the temporal impulse response of amplifier chain (usually dominated by the impulse response of the BPF).

Figure 9:
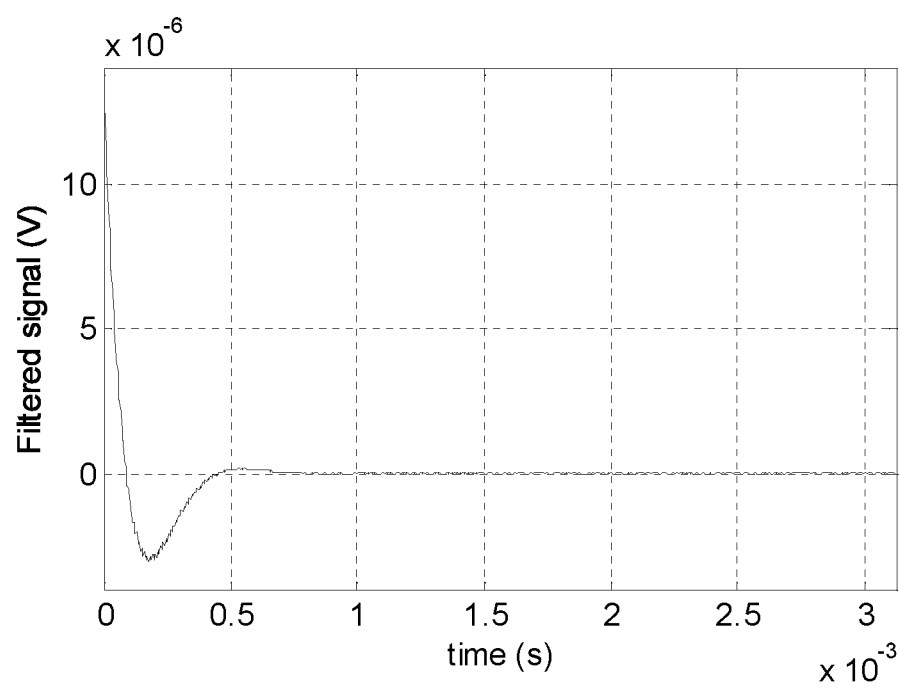
FIG. 9 is a plot of the signal output of a band-pass filter according to an example of this disclosure.

FIG. 9 shows a plot simulating the first 3 milliseconds (ms) of signal coming out of the band pass filter output. The simulation also includes an abrupt increase in ambient light from 0 to 100 times the amplitude of the optical emitter signals, resulting in an abrupt transient from t=0 to approximately 0.7 milliseconds (ms).

Figure 10:
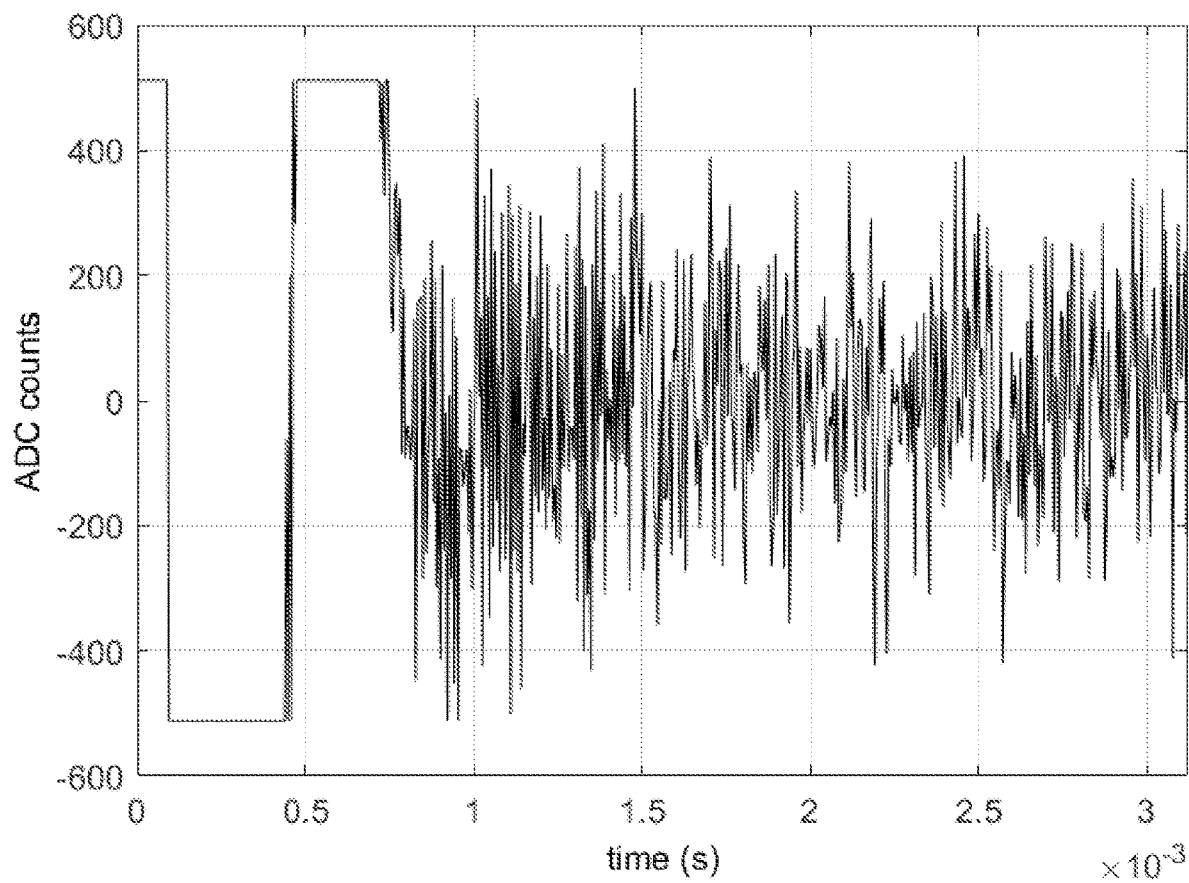
FIG. 10 is an example plot of the digitized band-pass filter output, showing that the data is sampled correctly after the first 0.7 millisecond (ms) of transient data.

FIG. 10 shows what happens to the transient, for example as provided in FIG. 9, and subsequent signals after digitization by a 10-bit ADC. The large voltage swings are clipped by the ADC while the signal remains in range. The system can be vulnerable to large and fast changes in ambient light, but the problem can be mitigated by: 1) detecting analog-to-digital converter saturation (either very large of very low counts) and 2) waiting a transient time, for example about 0.7 milliseconds (ms), for the transient to go away. In general, the maximum transient time is dictated by $f_{LP}$, the lowest passing frequency of the BPF and, as a rule-of-thumb, it is given by 0.35/$f_{LP}$. Once the transient is detected, the spread-spectrum sequence is corrupted. Therefore, the sequence should be discarded and the system can restart a new sequence after ADC high or low saturation is detected.

Figure 11:
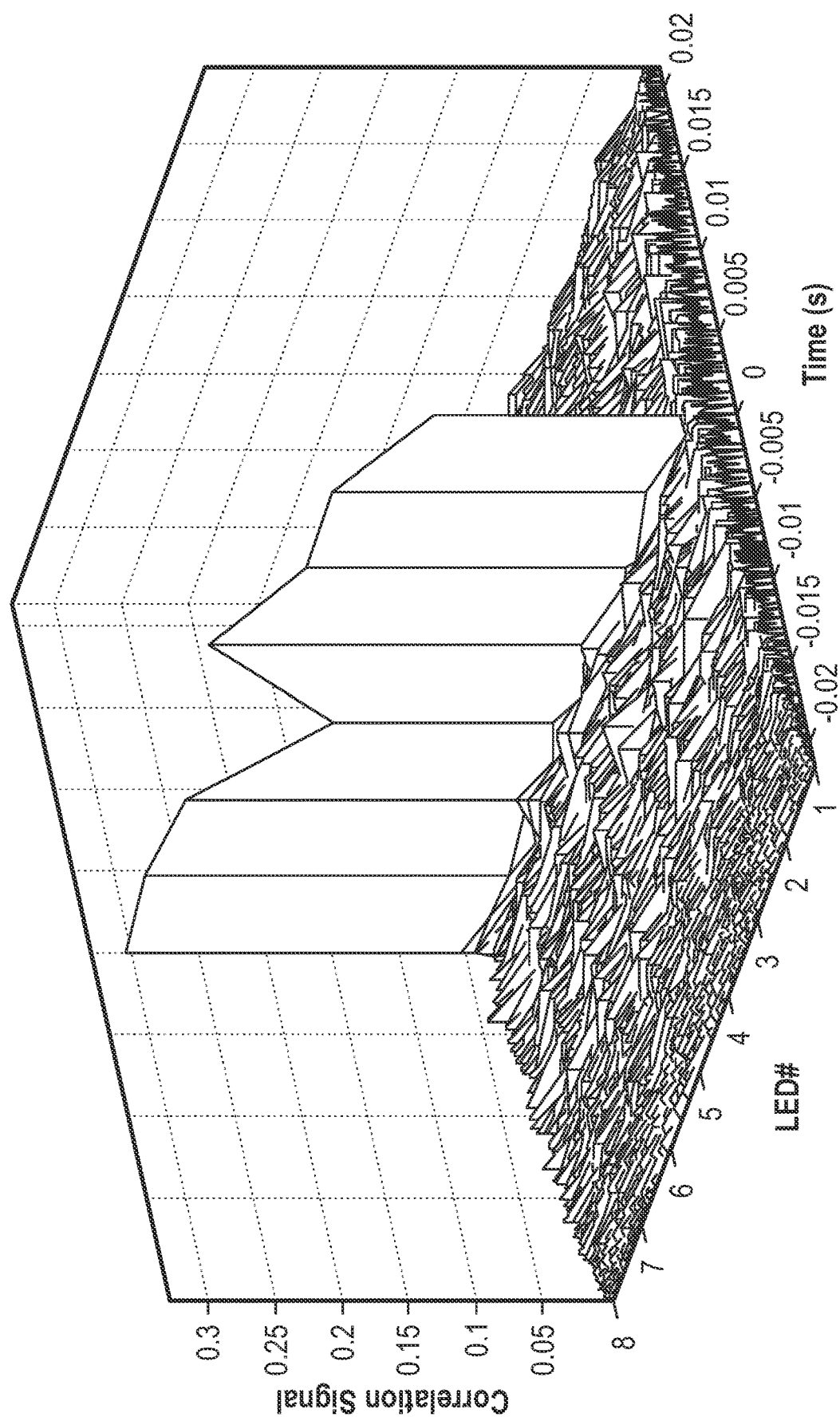
FIG. 11 is a plot of a cross-correlation of an emitted and detected pseudorandom number sequence according to an example of this disclosure.

FIG. 11 shows a plot of the simulated signal obtained when the emitted pseudorandom number sequence is cross-correlated with the detected sequence in eight emitters (eight LEDs in this example). As shown in FIG. 11, a strong correlation peak can be demonstrated when the sequences substantially match in time, corresponding to a large processing gain. The emitted sequence shown in FIG. 11 is the same as that depicted in FIG. 4, and the detected sequence shown in FIG. 11 is the same as that depicted in FIG. 10. The cross-correlation can show a strong peak when the time delay between the two sequences is substantially zero, the peak amplitude being proportional to $\Sigma(c_k)^2$. In other examples, the cross-correlation shows a strong peak only when the time delay between the two sequences is zero. This shows that 1) the N sequences are orthogonal, and 2) the spread-spectrum cross-correlation operable to generate the processing gain required to boost the signal over noise and ambient light interference. In the example shown in FIG. 11, the noise is 20 dB below the signal, ambient light is simulated as a DC component 26 dB above the signal amplitude, plus an AC component at 120 Hz and 3 dB above the signal amplitude. The resulting cross-correlation peak is, on average, 28 dB above the noise floor.

Figure 12:
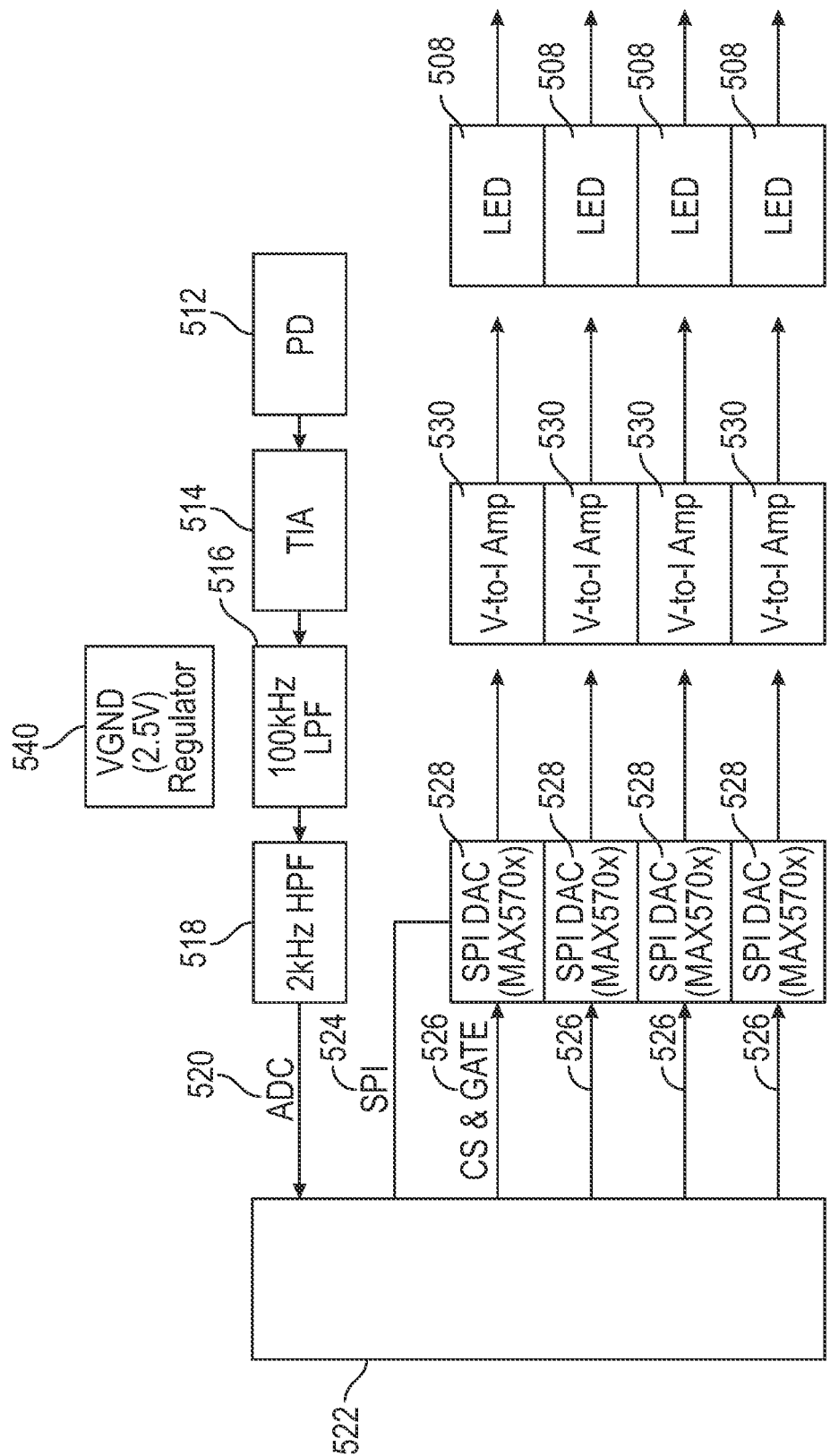
FIG. 12 is a schematic diagram depicting a 4-channel implementation of the system of FIG. 1.

The diagram in FIG. 12 depicts a 4-channel practical implementation of the system described in FIG. 1. In this example, the TIA 514 is used in place of the low noise amplifier 116, and the TIA is followed by a low-pass filter (LPF) 516 with a cutoff frequency, for example at 100 kHz, and a high-pass filter (HPF) 518 with a cutoff frequency, for example at 2 kHz. In combination, the TIA, LPF, and HPF form a band-pass filter that blocks all signals outside the desired frequency range, for example 2 kHz to 100 kHz. The LPF cutoff is chosen so that all frequency components pass all the way up to about half the sampling frequency, whereby aliasing is prevented, whereas the HPF cutoff is chosen high enough to block out-of-band noise while preventing $f_{LP}$ from getting too low. The microprocessor 522 includes an ADC 520 and 4 chip select (CS) and Gate lines 526 that control the timing of the digital-to-analog converters (DAC) 528. The digital signal level emitted by each optical emitter is transmitted to the DACs 528 using the serial peripheral interface (SPI) 524. The resulting output voltages are converted into currents by the voltage to current amplifiers (V-to-I Amps) 530. Finally, the output currents are used to drive four LEDs 508, used as the optical emitters.

Figure 13:
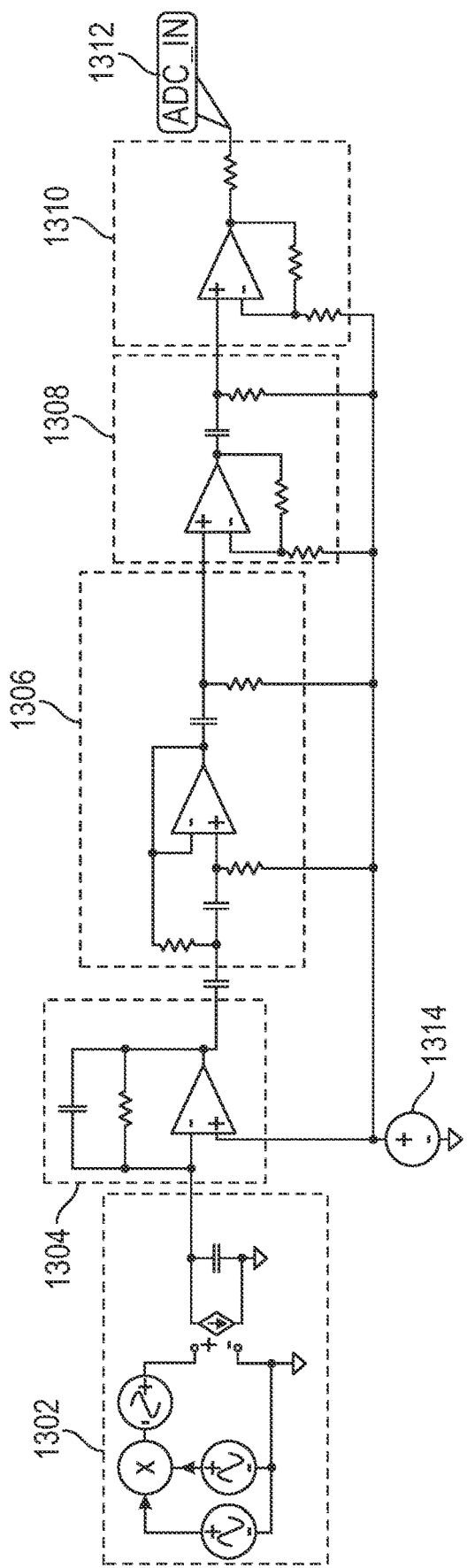
FIG. 13 is a schematic diagram of the electronic circuit of an analog front end circuit used for digital signal detection according to an example of this disclosure.

FIG. 13 shows a schematic diagram of the analog front end (AFE) circuit used for detecting the emitted signals. The circuit segment 1302 simulates the photocurrent signal generated by the photodetector 114. In the example shown in FIG. 13, the low noise amplifier and band pass filter are split into 4 stages. The first stage can include a TIA 1304 that converts the current signal generated by the photodetector into a voltage signal that is then filtered by the next stage. The next stage can be a filter 1306, for example an active Butterworth filter, that generates a band-pass filtered signal that is then amplified by the next two stages 1308, 1310. The next two stages 1308, 1310 can include non-inverting op-amps 1308, 1310 operable to generate the gain needed to place the voltage signal within the range of the analog-to-digital converter, and also the non-inverting op-amps 1308, 1310 can provide a low-impedance output into the analog-to-digital converter 1312, facilitating its operation.

Low noise operational amplifiers are used in all stages, providing low-noise operation. In one example, operational amplifiers from TEXAS INSTRUMENTS can be implemented and are generally identified by OPA part numbers. Limiting the number of amplifiers to 4 also enables simplified implementation using quad packages (that is, all 4 amplifiers present in a single integrated circuit package). The op-amps operate on a power supply, for example a 2.5V supply. The analog-to-digital converter 1312 also operates using this same supply or its integrated 2.5V reference. Having the voltages of the op-amps 1308, 1310 match is very convenient for the circuit design and prevents having to design additional features (overvoltage protection, DC realignment, etc.) that would add complexity and amplifiers to the design. One consequence of the 2.5V supply voltage 1302 is the necessary production of a midscale "virtual ground" 1314 to enable single-supply operation of the op-amps. This virtual ground 1314 can be located between the real rails (0V, 2.5V) of the op-amps 1308, 1310. Note that having the virtual ground 1314 be exactly the center code of the ADC is not critical since an offset in the bias would result in a DC offset of the detected sequence. The DC offset can be easily subtracted digitally by the processor before performing the cross-correlation.

The basic structure of a transimpedance amplifier 1304 reverse biases the photodiode by an amount equivalent to the virtual ground voltage 1314 of the TIA 1304. In the present example, the reverse biasing can be 1.25V. Therefore, a reduction in the capacitance of the photodiode is generated as compared to no-bias operation. The circuit design contains two (in at least one example, identical) gain stages because the gain-bandwidth product of the op-amps (5.5 MHz) is too low to amplify such a high-bandwidth (~100 kHz) signal to the necessary full-scale voltage in just one stage.

Figure 14:
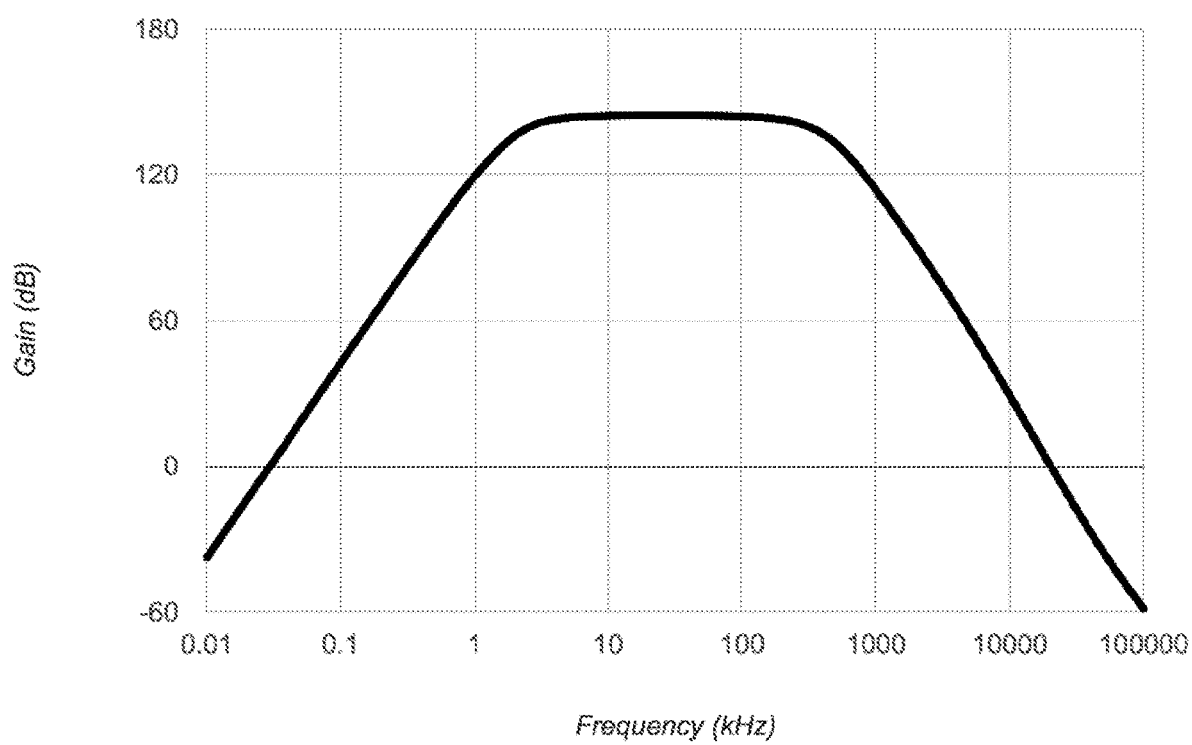
FIG. 14 is a plot of the frequency response of a band-pass filter, according to an example of this disclosure.

FIG. 14 shows a plot of a photodiode AFE gain. The plot shown in FIG. 14 shows the resulting band pass filter after signal propagation through all stages. The figure shows a low frequency 3 dB cutoff of about 2 kHz and a high frequency 3 dB cutoff of about 100 kHz. The low frequency should be as high as possible to reduce noise and to reduce the filter transient time, but high enough to pass all frequencies within the signal of interest. The high frequency should be high enough to pass all frequencies of the signal of interest but, to prevent aliasing, never larger than half the sampling frequency. The plot also demonstrates a large in-band gain (for example, >10 M), as needed to boost the detected signal into the operating range of voltages of the analog-to-digital converter.

The high-pass characteristic is provided by explicit active and passive filters. The low-pass characteristic is provided explicitly by TIA and implicitly by the natural roll-off behavior of the selected op-amps.

The effectiveness of the analog front end can be demonstrated by a simulation, the results of which are presented in FIGS. 15 and 16. The simulated input signal includes two ambient light components: a DC signal 100× stronger than the light emitting diode signal and a medium ambient light signal component at a frequency, for example 120 Hz. The signal of interest is a square wave varying at a frequency of 50 kHz. This signal is initially off and it is active starting at a time, for example approximately 42.5 ms. FIGS. 15A-D illustrate voltage levels over a predetermined period of time. The individual voltages shown are from different points from FIG. 13.

Figure 15A:
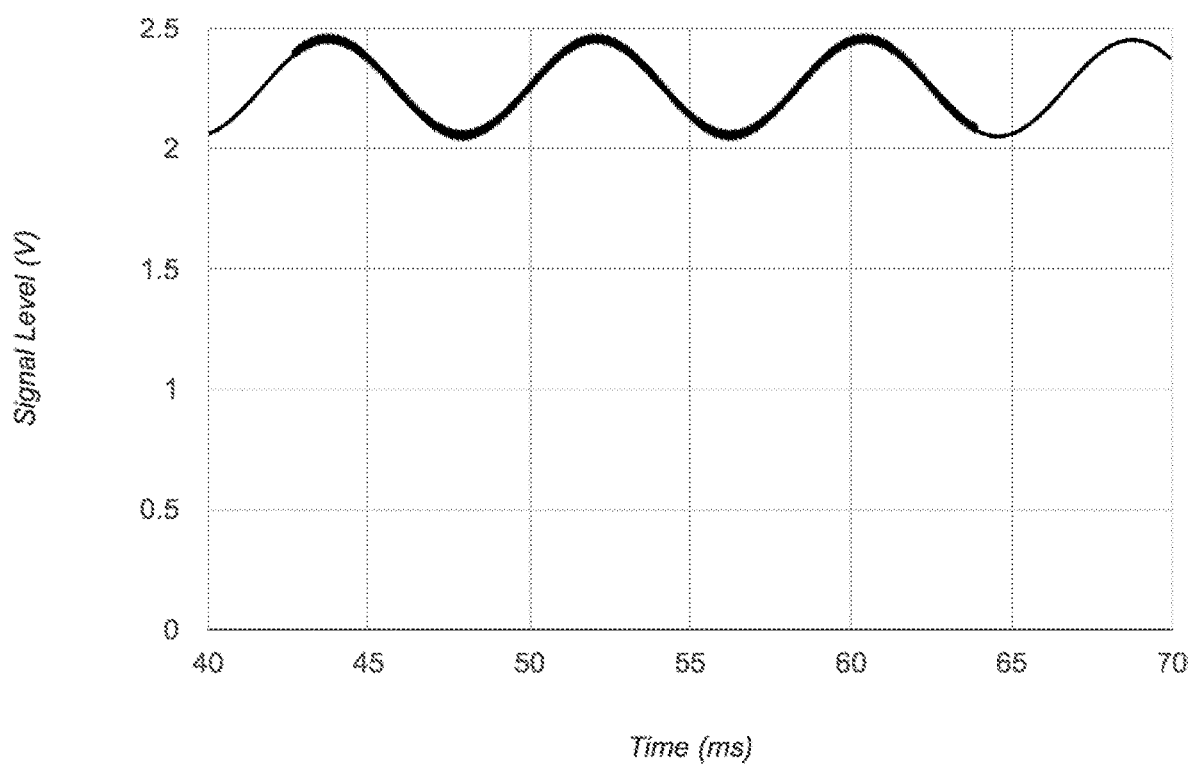
FIGS. 15A-D are example plots of a time-domain simulation of the signals labeled on FIG. 13.
Figure 15B:
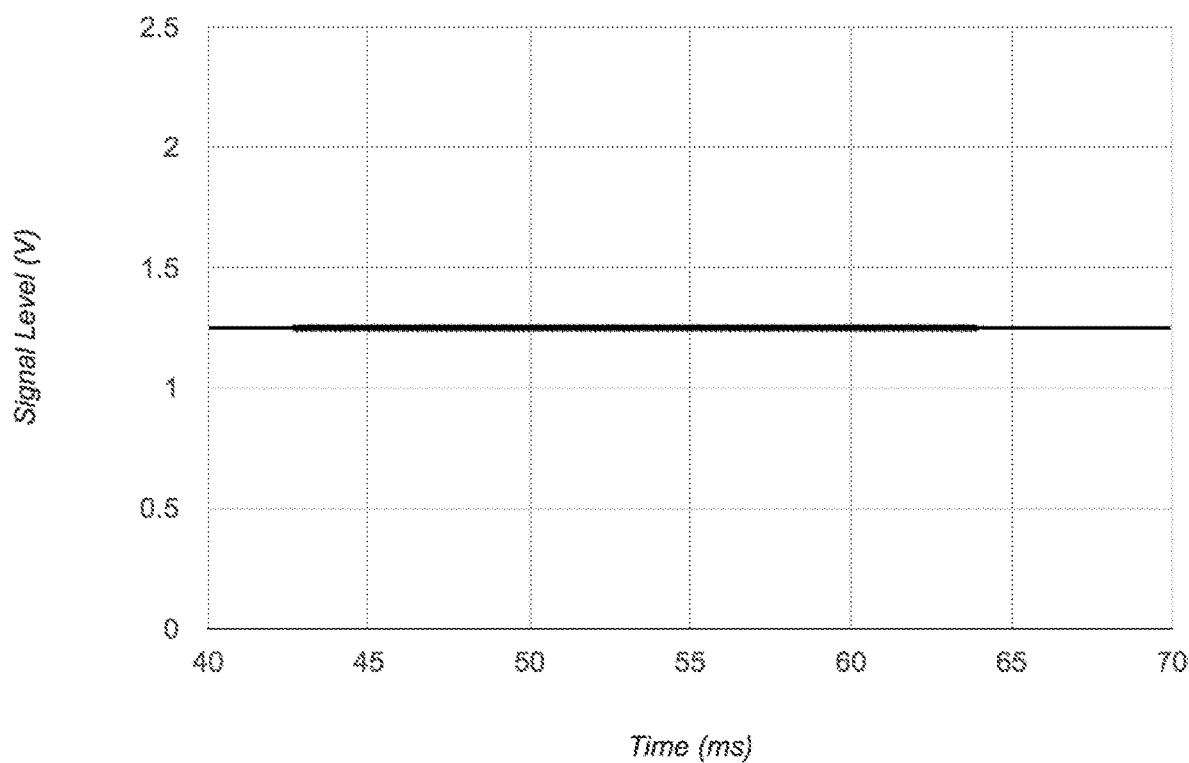
Figure 15C:
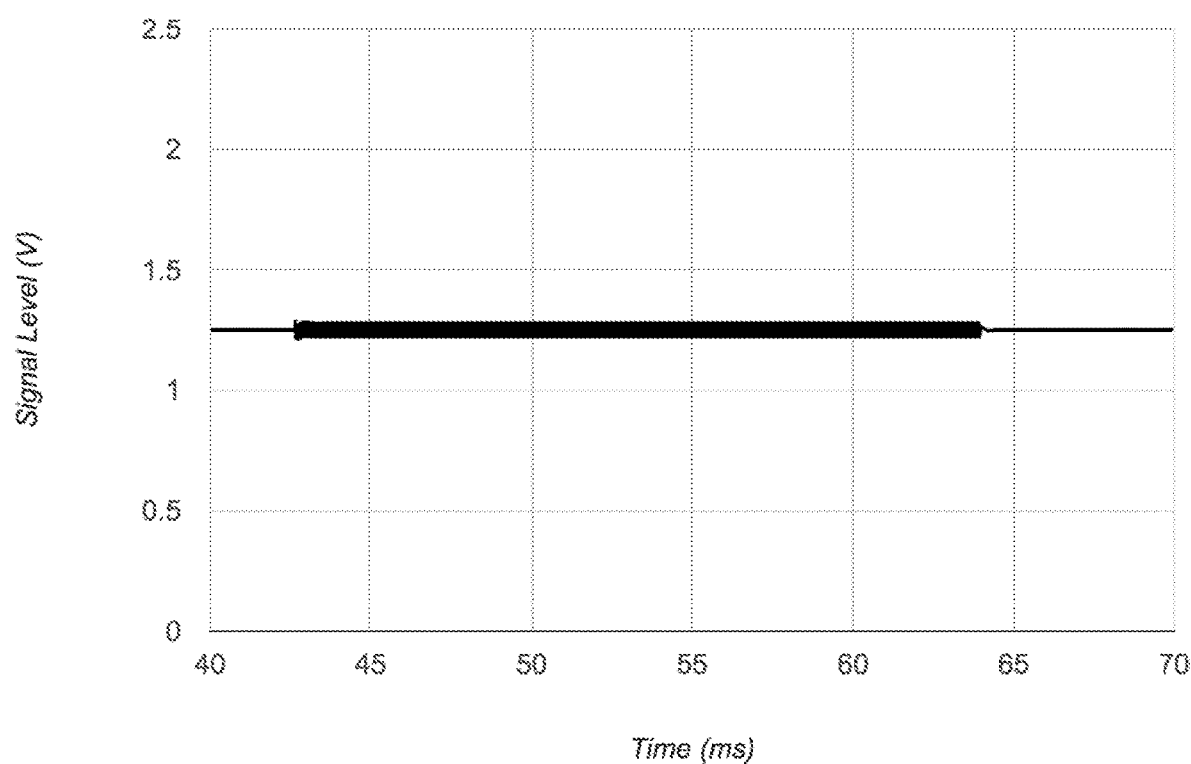
Figure 15D:
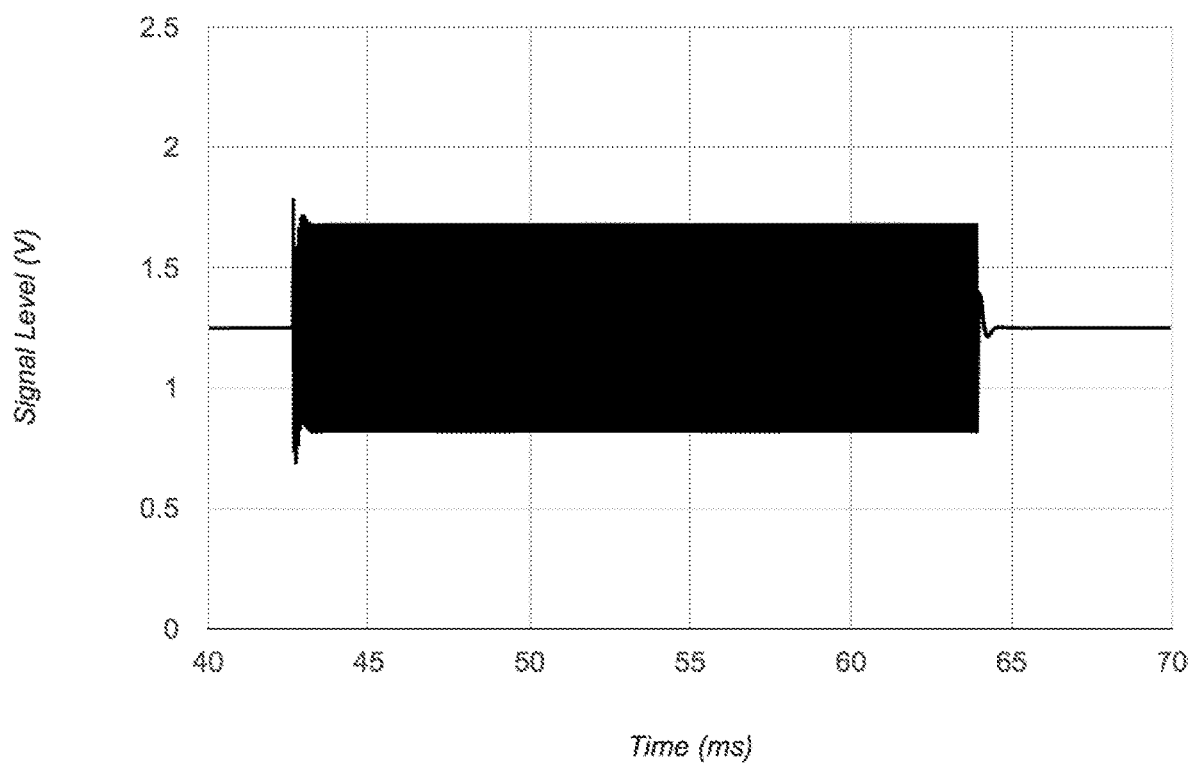
Figure 16A:
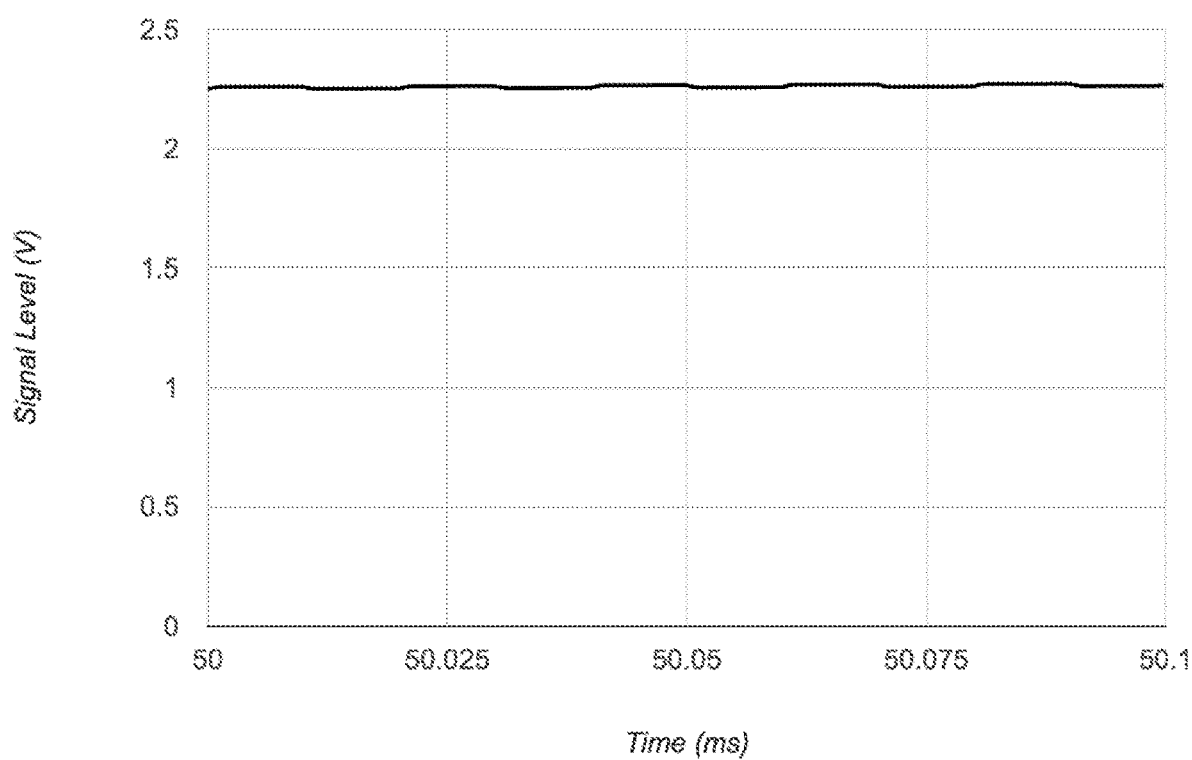
FIGS. 16A-D are example plots of the same time-domain simulation of FIG. 14, zoomed to a range of time spanning 0.1 ms.
Figure 16B:
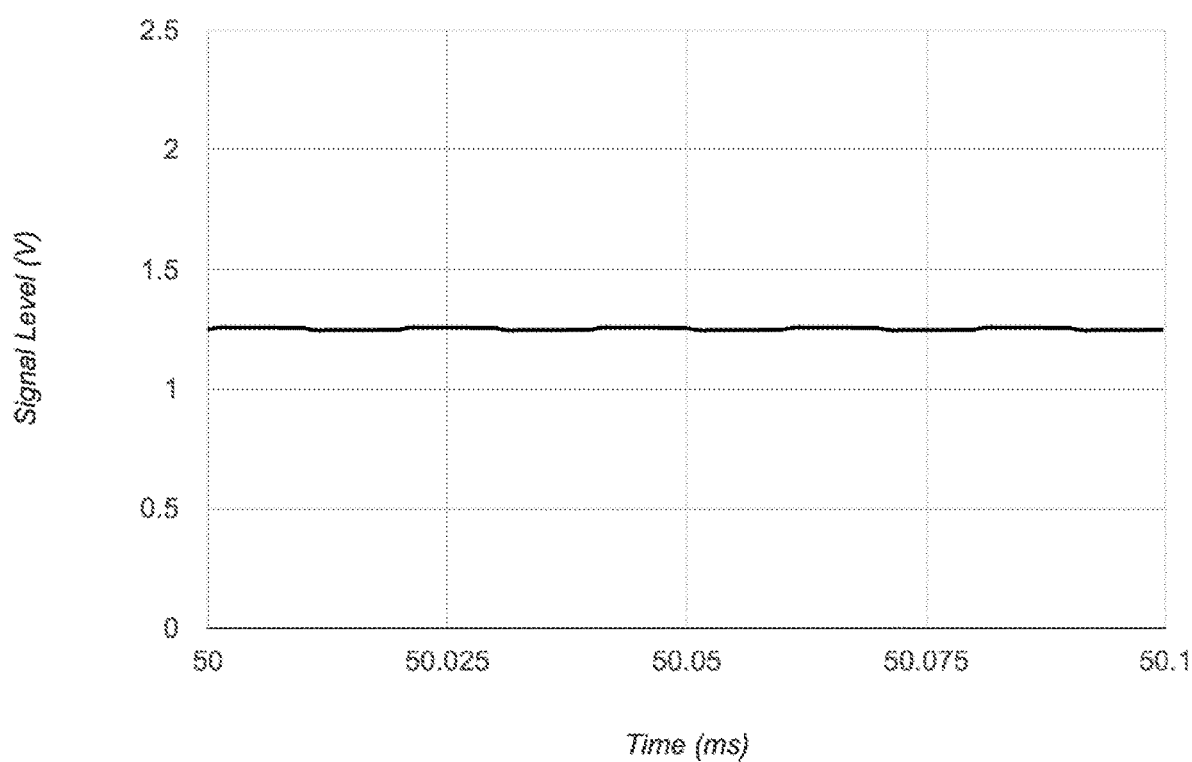
Figure 16C:
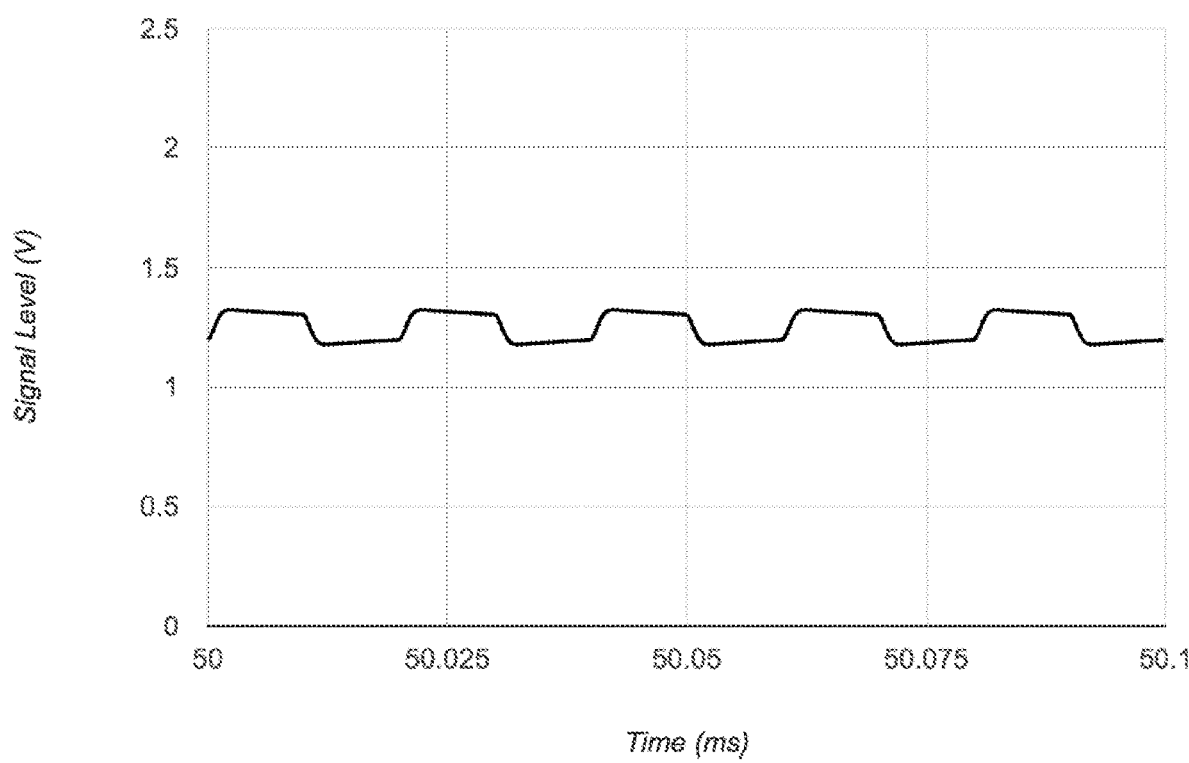
Figure 16D:
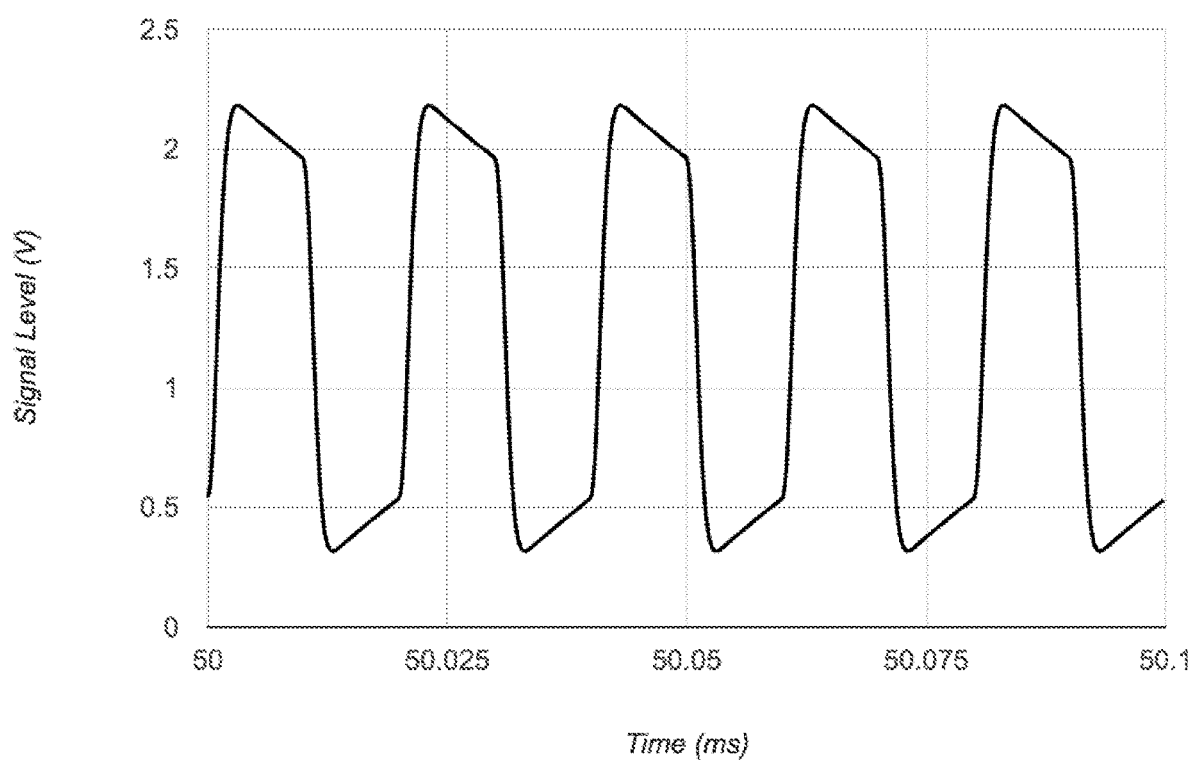

FIG. 15A illustrates a plot of a time-domain simulation of signal level in volts at point TIA, showing that the TIA output contains the DC and 120 Hz ambient light signals before bandpass-filtering. FIG. 15B illustrates a plot of a time-domain simulation of signal level in volts at point BUTTERWORTH, showing that the band-pass Butterworth filter has effectively blocked the DC and ambient light signal at 120 Hz. FIG. 15C illustrates a plot of a time-domain simulation of signal level in volts at point GAINS_1, showing partial amplification of the signal of interest before final amplification by Gain Stage 2. FIG. 15D illustrates a plot of a time-domain simulation of signal level in volts at the point indicated by ADC_IN, the final output of the analog front end. FIG. 15D shows that the ADC_IN signal is within a voltage range of, roughly, 400 mV and 2.1V suitable for effective analog-to-digital conversion using an ADC with a reference voltage, for example 2.5V for an ADC reference voltage of roughly 5V.

FIGS. 16A-D shows a zoom into 0.1 millisecond (ms) of the same signals shown in FIGS. 15A-D, showing the input square wave is effectively recovered at the end of a signal chain. For simplicity, the LED emitted sequence is represented by a square wave with a frequency close to the middle of the band of frequencies of interest (50 kHz). The analog front end output shows that the bit sequence was correctly conveyed to the output and the ambient light signal was correctly filtered out without causing saturation of the analog-to-digital converter. Note there is some droop in the square wave. The droop in the square wave is caused by the low-frequency cutoff of the band pass filter. This alteration of the sequence results in a drop in the correlation peak, but the drop is taken into account during calibration. During calibration, the expected value of the correlation peak in the presence of the droop and other device-dependent factors are known, such as actual gains and transfer functions of the analog front end and LED driver circuit. Therefore, during operation the detected peak is compared against the calibrated peak and tissue parameters are determined with respect to calibration.

Figure 17:
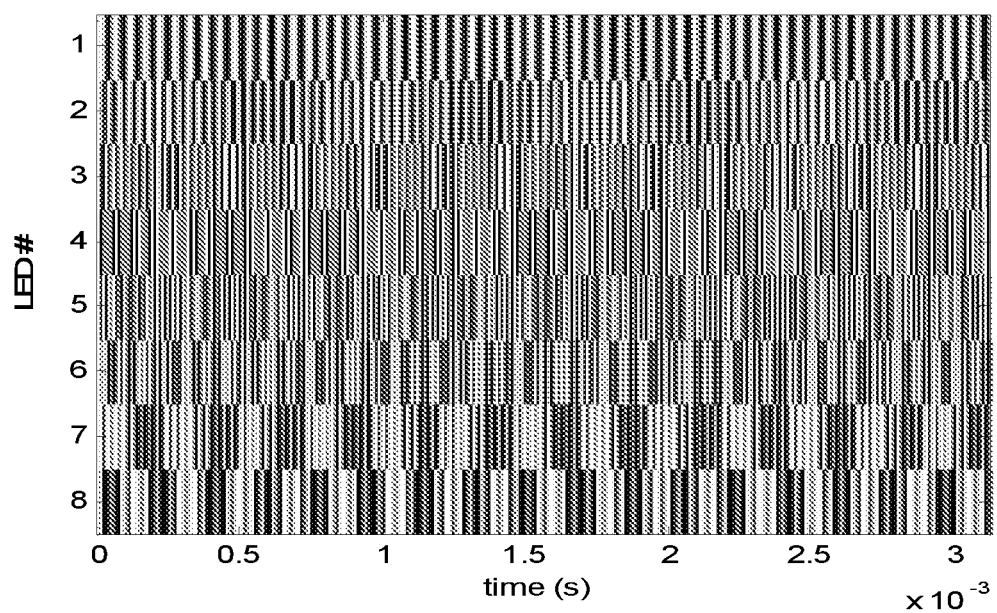
FIG. 17 is an example illustration eight narrow band sinusoidal signals that are used to modulate the LEDs of FIG. 1.
Figure 18:
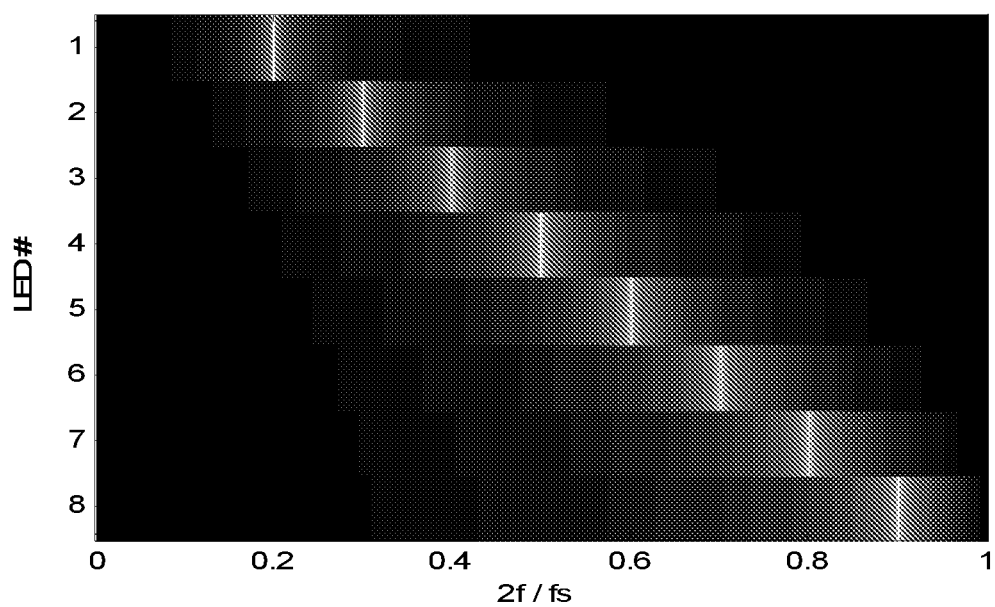
FIG. 18 is an example of resulting modulation spectrum in relation to what is shown in FIG. 17.
Figure 19:
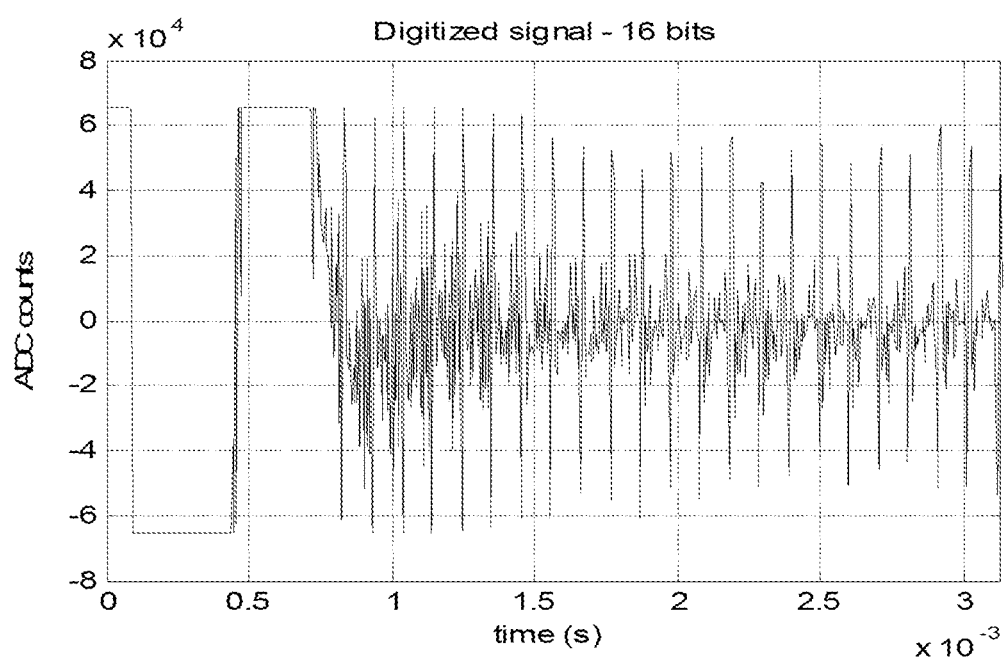
FIG. 19 is an example of detected and digitized signal from FIG. 18.
Figure 20:
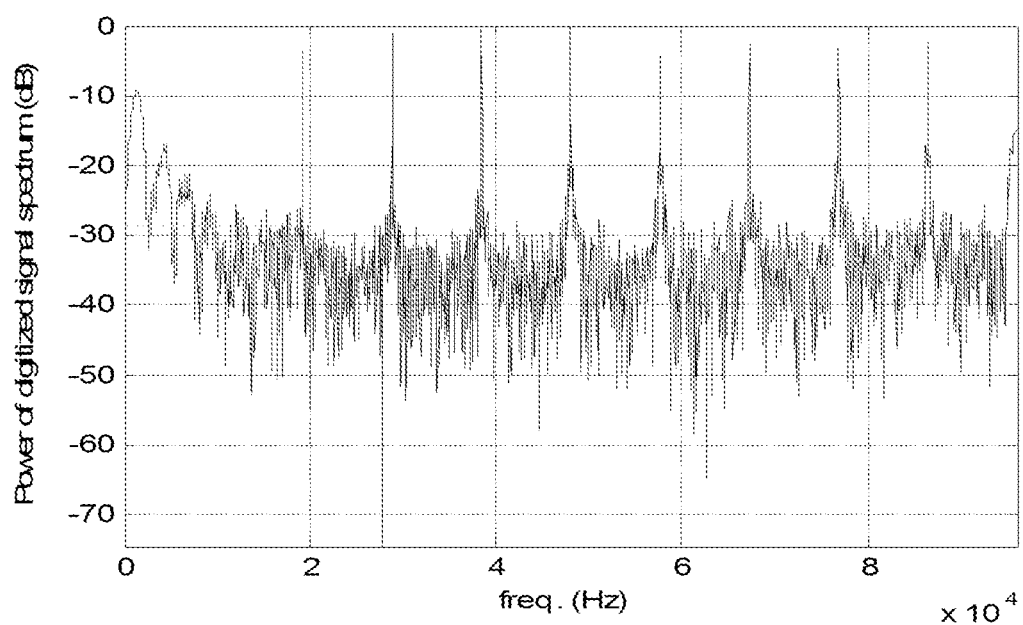
FIG. 20 is an example illustration of the detected signal containing a summation of all modulating frequencies.

Narrow-band high-frequency signals can also be used to separate the LED illumination from ambient light interference. FIG. 17 shows 8 narrow band sinusoidal signals that are used to modulate the LEDs of FIG. 1. In this example, the LEDs are modulated (turned on and off) with signals ranging in frequency from 19.2 kHz to 86.4 kHz in 9.6 kHz increments. The resulting modulation spectrum is shown in FIG. 18, showing that the signals from each of the 8 LEDs are indeed orthogonal in frequency, allowing them to illuminate simultaneously and be demodulated after detection. FIG. 19 shows the detected and digitized signal. After the first predetermined time, for example 0.7 milliseconds (ms), of saturation (due to the LPF temporal transient), the detected signal contains a summation of all modulating frequencies, as shown more clearly in the spectrum depicted in FIG. 20, showing all the individual tones used to modulate each LED as spectral peaks. Then, signal demodulation is performed by digitally multiplying the detected and digitized signal by each one of the 8 modulating frequencies, following by low-pass filtering to remove the frequency-doubling components.

Figure 21A:
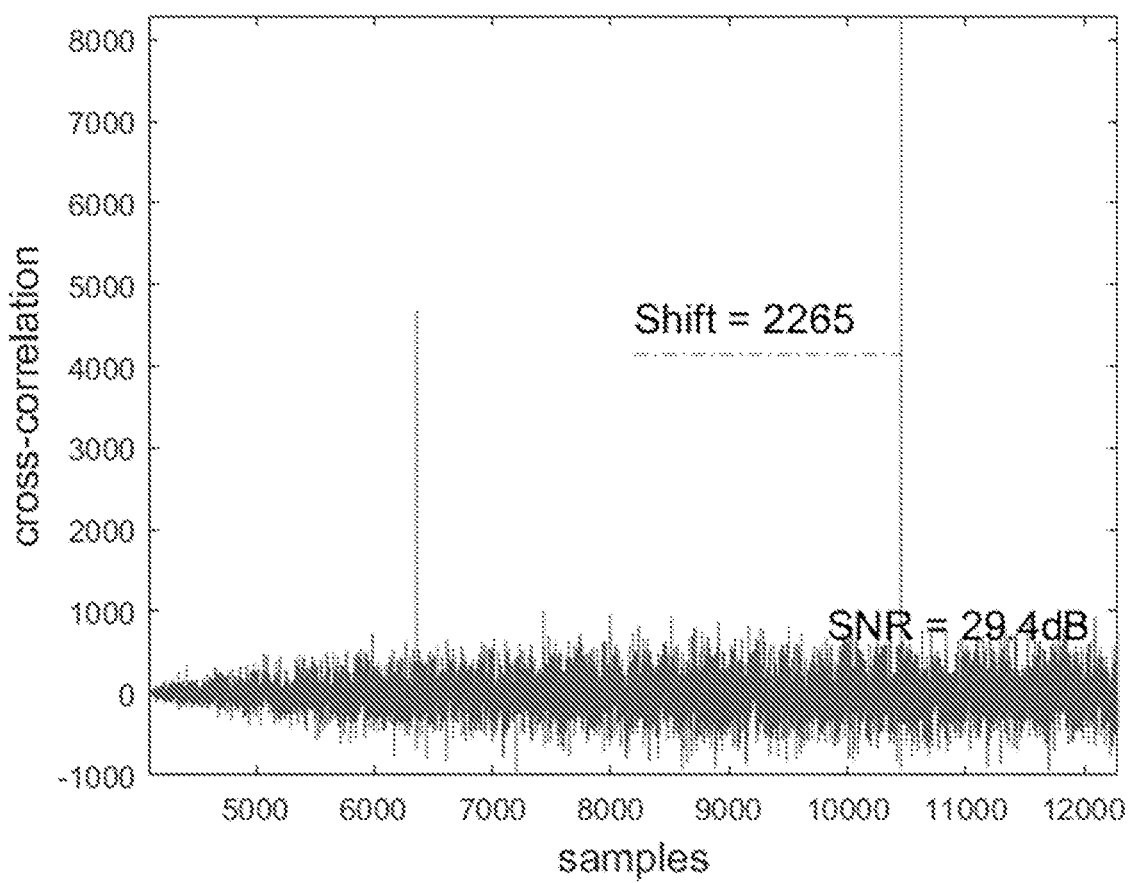
FIG. 21A is an example plot of two correlation peaks using the system of FIG. 12.
Figure 21B:
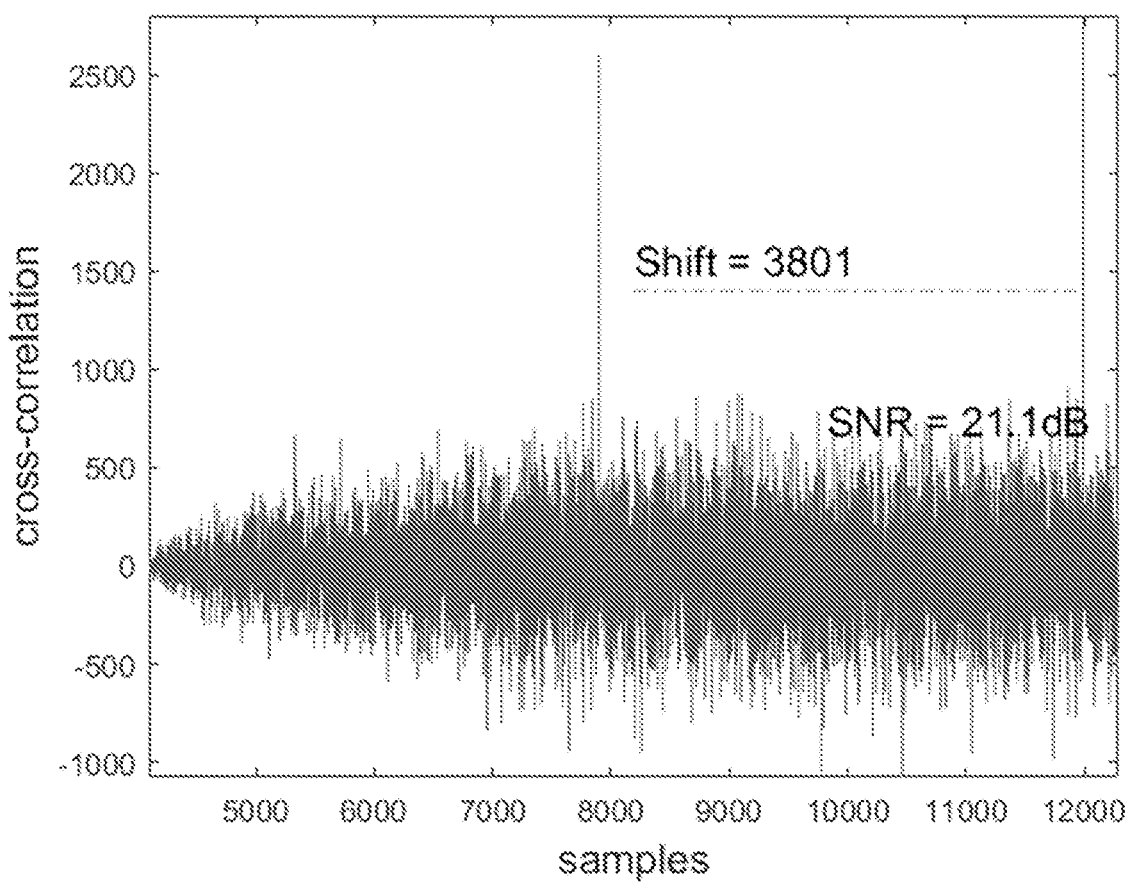
FIG. 21B is another example plot of two correlation peaks using the system of FIG. 12.

FIGS. 21A and 21B and the following discussion illustrate an experimental demonstration of the disclosure in operation. A board was fabricated capable of implementing the electronic diagrams shown in FIGS. 12 and 13. The board included four LEDs: two LEDs at a distance of 15 mm and two at a distance of 27 mm to the photodetector. The microprocessor in the board was programmed to generate a 12-bit binary maximum length sequence. The sequence is 4095 bits long. Since the signal only adds up in phase when perfectly aligned, the maximum improvement in SNR at the correlation peak is given by $\Sigma(c_k)^2/\Sigma(ck)=4095=36.1$ dB. During each instance of tissue monitoring, two repetitions of the sequence are being transmitted and detected at a time, thus guaranteeing that the sequence is completely detected at least once per monitoring event.

The board was cut down to a narrow width of 15 mm and was placed on the wrist of a healthy adult male with Fitzpatrick skin type II, thus corresponding to the condition of a narrow wearable band worn in a user's wrist. Then data was collected in two modes, indoors and outdoors, while monitoring data from one of the LEDs at the 27 mm distance—the worst-case scenario given light absorption by tissue. The LED peak wavelength was 970 nm.

FIG. 20A illustrates an indoor case with two correlation peaks. FIG. 20A shows the result of the cross-correlation of the ADC output with the broadband pseudorandom signal 704. This cross-correlation clearly shows two peaks, thus being an experimental demonstration of the peak 708 shown in FIG. 7. To avoid complications in signal synchronization, transmission of two sequences were made during each monitoring event, thus assuring that at least one of them would be completely detected, even though the exact offset would not be known until after detection. The first peak is only partially overlapped with the pseudorandom sequence and consequently it presents a lower amplitude, while the second sequence completely overlaps and shows a higher peak correlation amplitude at an offset of 2265 samples. The SNR can be calculated from the ratio of the highest peak power to the power in the signal skirt (the mean signal power in the fuzzy region away from the peak). In this example, the SNR has a value of 29.4 dB. The 6.7 dB difference with respect to the maximum possible SNR can be explained by imperfections in data collection (for example, motion, ambient light) but, in the indoor case, it is mostly due to noise in the detected signal, which is dominated by shot noise in the optical signal emitted by the LED.

FIG. 20B illustrates an outdoor case with two correlation peaks. When moving outdoors ambient light clearly dominates the signal of interest, and it also generates its own shot noise in addition to that generated by the LED. Moreover, Sun light is rich in visible and infrared spectral components, providing more light interference through tissue than what would be expected from any typical indoor illumination source. FIG. 20B shows the correlation peaks obtained during monitoring under full Sun exposure in a clear day close to noon in the Southwestern United States, at a latitude of 30.2° N and an elevation of approximately 489 feet. The SNR dropped to 21.1 dB, meaning that the additional noise and interference caused a loss of 8.3 dB in SNR. Nevertheless, the correlation peak still is clearly above the noise floor even in this very demanding scenario (close to worst case) and it is providing us with an SNR that is sufficiently large for possibly any tissue monitoring algorithm, even before any temporal averaging or other signal processing is used to further improve the SNR, effectively demonstrating the ability of the present disclosure to overcome ambient light even in the most extraneous of circumstances.

Figure 22A:
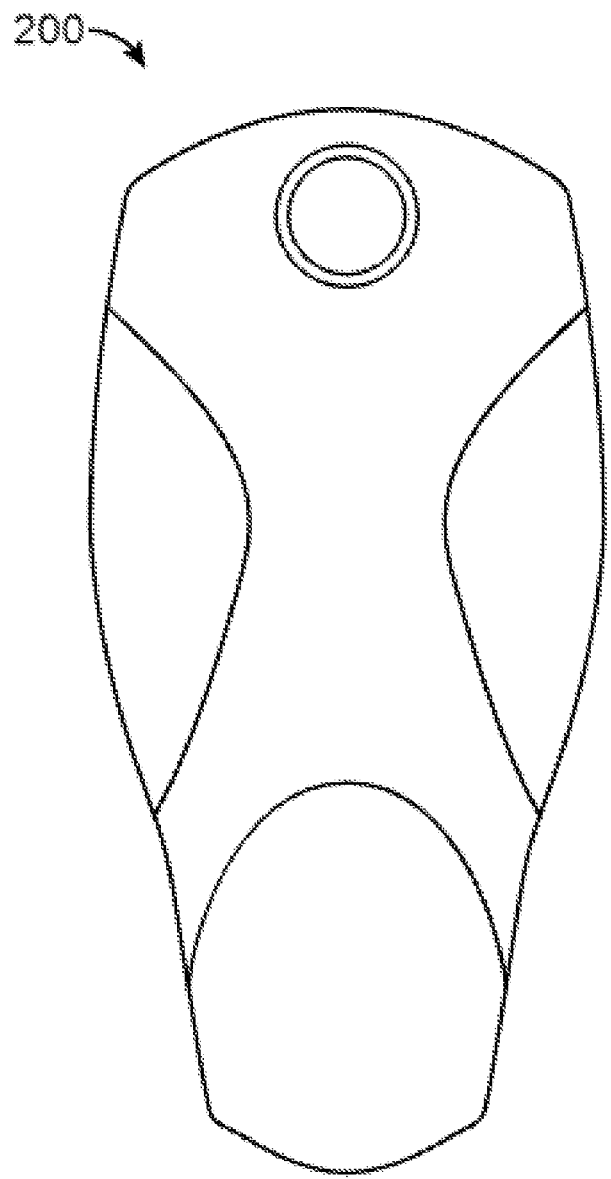
FIG. 22A is a schematic diagram of the front of a non-invasive optical-electronic device, according to an example of the present disclosure.
Figure 22B:
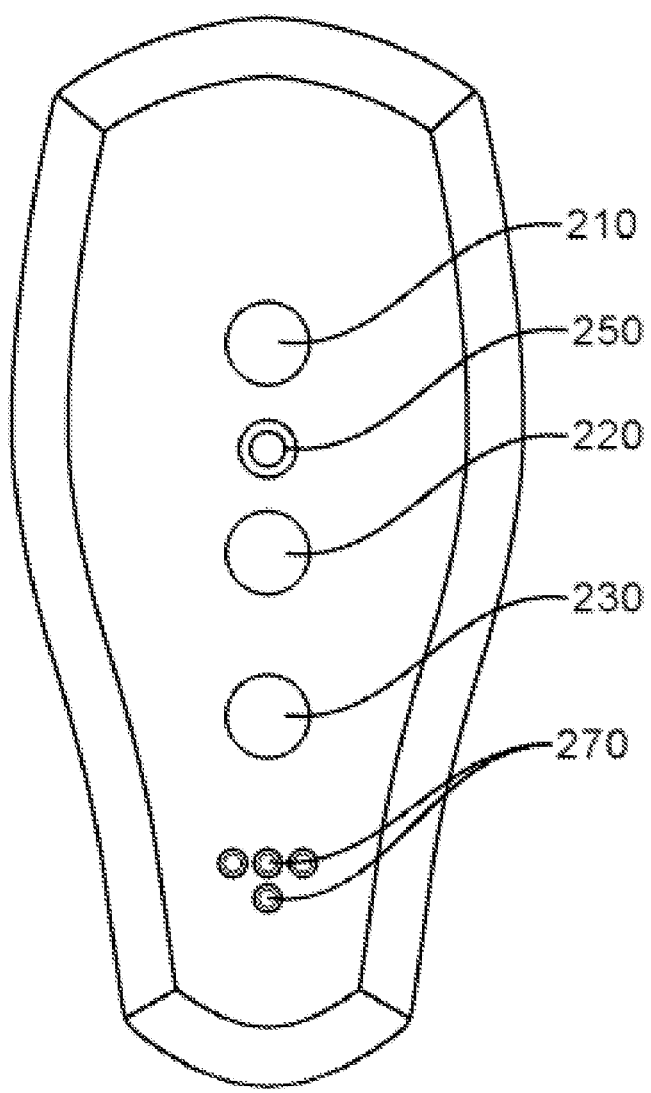
FIG. 22B is a schematic diagram of the back of a non-invasive optical-electronic device, according to an example of the present disclosure.
Figure 22C:
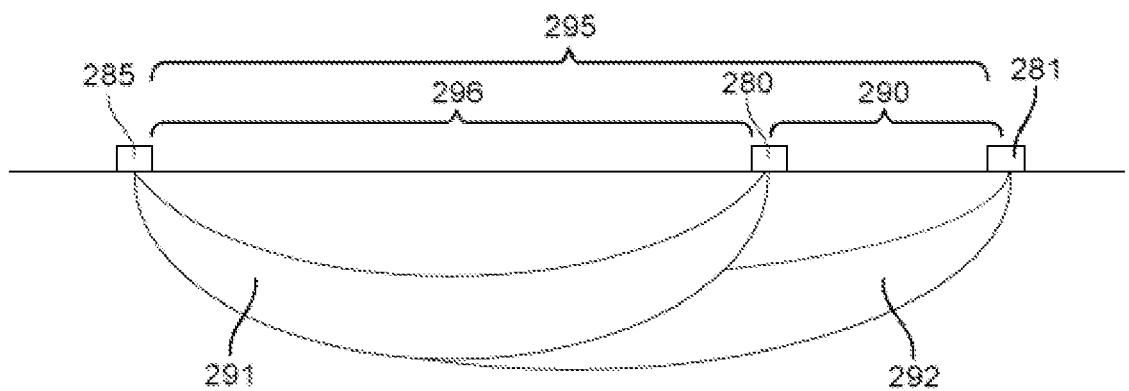
FIG. 22C is a schematic diagram of a spatially-resolved NIRS sensor that is included on a non-invasive optical-electronic device, according to an example of the present disclosure.

FIG. 22A-C illustrates a non-invasive optical-electronic device 200, according to an alternative example of this disclosure. The device 200 is operable to be placed either in contact or adjacent to tissue of interest. In one example, the device 200 can be worn on the wrist or other area. In still another example, the device 200 can be worn on a limb of a user, such as on the calf muscle of a user's leg or the bicep of a user's arm. In at least one example, the device 200 can be optimized for a given limb, thereby increasing accuracy of the device. In other examples, the device 200 can be optimized based on the location of a user's body that the device 200 will be in contact with. In other examples, the device 200 can be optimized based on the size, gender, or age of the user. In still other examples, a variety of the above optimizations can be implemented for a given device. FIG. 22A illustrates the front of the optical-electronic device. FIG. 22B illustrates the back of the optical-electronic device, including emitters 220, 230, 250 and photodetector 210. The device 200 also includes data and charging contacts 270. In at least one example, the data and charging contacts 270 can be used to electrically detect if the sensor is making contact with the skin of a user. The presence of multiple emitters 220, 230, 250 on the optical-electronic device allows for spatially-resolved data gathering in real-time. The optical-electronic device 200 can be operable to determine the optical absorption of chromophores, such as water, hemoglobin in its multiple forms, including oxyhemoglobin ($HbO_2$), deoxyhemoglobin (HHb), oxymyoglobin, deoxymyoglobin, cytochrome c, lipids, melanins, lactate, glucose, or metabolites.

FIG. 22C illustrates a spatially-resolved near infrared spectrometry (NIRS) sensor that can be included on the non-invasive optical-electronic device 200, according to an example of the disclosure. As shown in FIG. 2C, the spatially-resolved NIRS sensor includes light emitters 280 and 281 which emit light that is scattered and partially absorbed by the tissue. Each emitter 280, 281 can be operable to emit a single wavelength of light or a single range of wavelengths. In at least one example, each emitter 280, 281 can be operable to emit at least two wavelengths of light or at least two ranges of wavelengths. Each emitter 280, 281 can include one or more LEDs or light sources. Each emitter 280, 281 can include a low-powered laser, LED, or a quasi-monochromatic light source as a light source, or any combination thereof. Each emitter 280, 281 can also include a light filter.

A fraction of the light emitted by emitters 280 and 281 is detected by photodetector 285, as illustrated by the parabolic or "banana shaped" light arcs 291 and 292. Emitters 280, 281, are separated by a known distance 290, and therefore have different known spacings 295, 296 from the detector 285, and produce a signal that is later detected at photodetector 285. In at least one example, the known distance 290 between emitters 280, 281 can be about 12 millimeters. In at least one example, the 12 millimeter known distance between emitters 280 and 281 corresponds to a known spacing 295 of emitter 281 from detector 285 of 27 millimeters and a known spacing 296 of emitter 280 from detector 285 of 15 millimeters. In other examples, the spacings 295 and 296 can be between 5 millimeters and 50 millimeters. Other examples can include a spacing of 7.3 millimeters, 12.5 millimeters, and 17.7 millimeters. In other examples, the known distance can be selected based on a variety of factors, which can include the wavelength of the light, the tissue involved, or the age of the user. While FIG. 22C depicts emitters 280, 281 arranged in a row and longitudinally spaced such that known distance 290 corresponds to a difference in the spacing between emitters 280, 281 and photodetector 285, the emitters can be spaced in any configuration so long as at least two of the emitters are spaced at different distances from photodetector 285.

The optical-electronic device 200 disclosed herein can have different amounts of emitters and photodetectors without departing from the principles of the present disclosure. Further, the emitters and photodetectors can be interchanged without departing from the principles of the present disclosure. Additionally, the wavelengths produced by the light sources can be the same for each emitter or can be different.

In at least one example, the device 200 is used for the monitoring of physiological parameters of a user during a physical activity. Use of the device 200 can be relevant in endurance type sports, such as running, cycling, multisport competition, rowing, but can also be used in other physical activities and for tracking overall fitness level, physiological level and tissue hydration. The device 200 can be operable to wirelessly measure real-time muscle parameters during physical exercise. The device 200 can be secured to a selected muscle group of the user, such as the leg muscles of the vastus lateralis or gastrocnemius, which are primary muscle groups of running and cycling. Furthermore, the device can be provided or worn at sites that do not present any significant muscle groups and which are commonly illuminated by ambient light, including the wrist, forearm and arm. Additionally, the device can be used as a wearable device, worn by active or sedentary users, outdoors or indoors, exposed to direct or indirect Sun light or artificial lighting, including a combination of LED light sources, fluorescence, incandescent and halogen light sources. The location of the device can make the features of the present disclosure advantageous to prevent noise from preventing accurate measurements. Furthermore, some sites, such as the wrist, are less optically dense in the near-infrared region of light and are therefore less capable of effectively blocking ambient light, further increasing the importance of the present subject matter.

Figure 23:
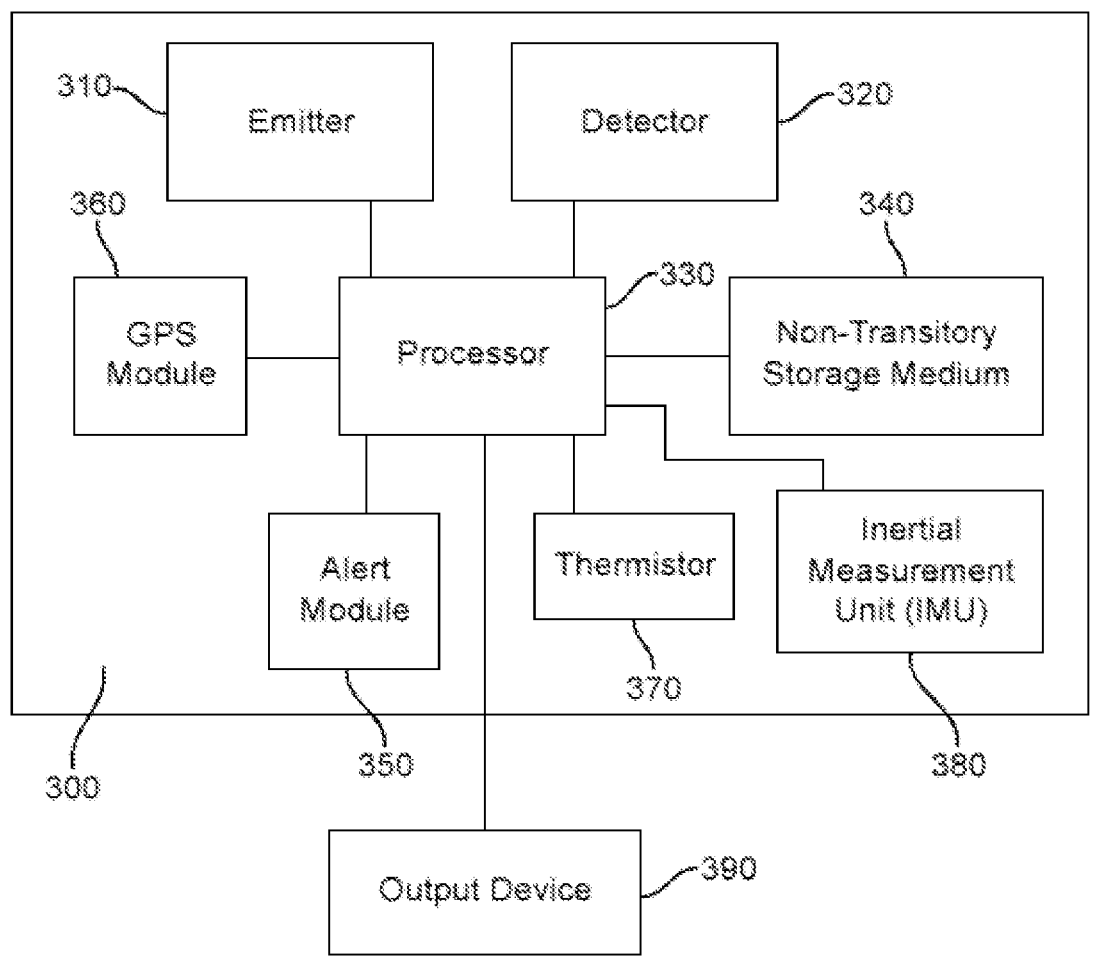
FIG. 23 illustrates the components of an optical-electronic device, according to an example of the present disclosure.

FIG. 23 illustrates the components of an optical-electronic device 300 according to an example of this disclosure. As shown in FIG. 23, the optical-electronic device includes an emitter 310 and detector 320, which are coupled to a processor 330. The processor 330 is coupled to a non-transitory storage medium 340. The device 300 is coupled to an output device 390.

The emitter 310 delivers light to the tissue and the detector 320 collects the optically attenuated signal that is back-scattered from the tissue. In at least one example, the emitter 310 can be operable to emit a predetermined number of wavelengths of light, for example at least three separate wavelengths of light. In another example, the emitter 310 can be operable to emit bands or ranges of wavelengths, for example at least three separate bands or ranges of wavelengths. In at least one example, the emitter 310 can include one or more light emitting diodes (LEDs) or light sources. The emitter 310 can also include a light filter. The emitter 310 can include a low-powered laser, LED, or a quasi-monochromatic light source, or any combination thereof, as a light source. The emitter 310 can emit light ranging from infrared to ultraviolet light. As indicated above, the present disclosure uses NIRS as a primary example and the other types of light can be implemented in other examples and the description as it relates to NIRS does not limit the present disclosure in any way to prevent the use of the other wavelengths of light.

The data generated by the detector 320 can be processed by the processor 330, such as a computer processor, according to instructions stored in the non-transitory storage medium 340 coupled to the processor 330. The processed data can be communicated to the output device 390 for storage or display to a user. The displayed processed data can be manipulated by the user using control buttons or touch screen controls on the output device 390.

The optical-electronic device 300 can include an alert module 350 operable to generate an alert. The processor 330 can send the alert to the output device 390 indirectly, for example through an application or a cloud-based program, or the alert module 350 can send the alert directly to the output device 390, for example by a wire, radio signal, or BLUETOOTH. In at least one example, the optical-electronic device 300 can be operable so that the processor 330 is operable to send an alert to the output device 390 without the device including an alert module 350.

The alert can provide notice to a user, via a speaker or display on the output device 390, of a change in biological indicator conditions or other parameter being monitored by the device 300, or the alert can be used to provide an updated biological indicator level to a user. In at least one example, the alert can be manifested as an auditory signal, a visual signal, a vibratory signal, or combinations thereof. In at least one example, an alert can be sent by the processor 330 when a predetermined biological indicator event occurs during a physical activity.

In at least one example, the optical-electronic device 300 can include a Global Positioning System (GPS) module 360 operable to determine geographic position and tagging the biological indicator data with location-specific information. The optical-electronic device 300 can also include a thermistor 370 and an inertial measurement unit (IMU) 380. The inertial measurement unit (IMU) 380 can be used to measure, for example, gait performance of a runner or pedal kinematics of a cyclist, as well as physiological parameters of a user during a physical activity. The thermistor 370 and inertial measurement unit (IMU) 380 can also serve as independent sensors operable to independently measure parameters of physiological threshold. The thermistor 370 and inertial measurement unit (IMU) 380 can also be used in further algorithms to process or filter the optical signal.

Figure 24:
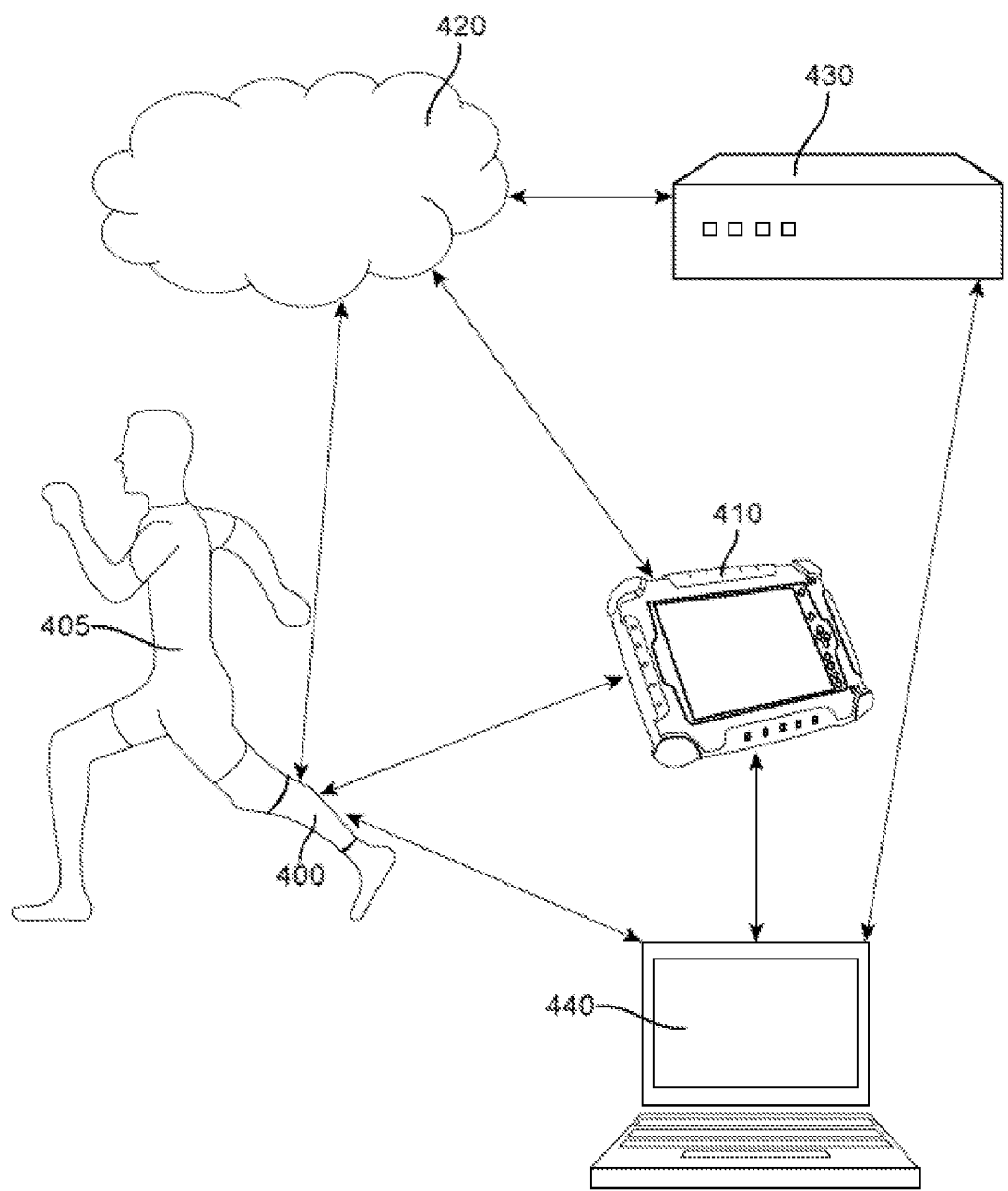
FIG. 24 illustrates an environment within which the noninvasive optical-electronic device can be implemented, according to an example of the present disclosure.

FIG. 24 illustrates an environment within which the noninvasive optical-electronic device 400 can be implemented, according to an example of this disclosure. As shown in FIG. 23, the optical-electronic device 400 is worn by a user to determine biological indicator levels during a physical activity. The optical-electronic device 400 is depicted as being worn on the calf of a user 405; in other examples, the optical-electronic device 400 can be worn on any portion of the user suitable for monitoring biological indicator levels such as the wrist or upper arm. The device 400 can be used with an output device 410, such as a smartphone (as shown), a smart watch, computer, mobile phone, tablet, an electronic processing and displaying unit, cloud storage, or a remote data repository via a cellular network or wireless Internet connection.

As shown in FIG. 24, the optical-electronic device 400 communicates with a output device 410 so that data collected by the optical-electronic device 400 is displayed or transferred to the output device 410 for communication of real-time biological indicator data to the user 405. In at least one example, an alert can be communicated from the device 400 to the output device 410 so that the user 405 can be notified of a biological indicator event. Communication between the device 400 and the output device 410 can be via a wireless technology, such as BLUETOOTH, infrared technology, or radio technology, or can be through a wire. Transfer of data between the optical-electronic device 400 and the output device 410 can also be via removable storage media, such as a secure digital (SD) card. In at least one example, a display unit can be substituted for the output device 410.

The optical-electronic device 400 also communicates with a personal computing device 440 or other device operable to store and/or display user-specific biological indicator data. The personal computing device 440 can include a desktop computer, laptop computer, tablet, smartphone, smart watch, or other similar device. Communication between the device 400 and the personal computing device 440 can be via a wireless technology, such as BLUETOOTH®, infrared technology, or radio technology. In other examples, the communication between the device 400 and the personal computing device 440 can be through a wire or other physical connection. Transfer of data between the optical-electronic device 400 and the personal computing device 440 can also be via removable storage media, such as an SD card.

The output device 410 can communicate with a server 430 via a network 420, allowing transfer of user-specific biological indicator data to the server 430. The output device 410 can also communicate user-specific biological indicator data to cloud-based computer services or cloud-based data clusters via the network 420. The output device 410 can also synchronize user-specific biological indicator data with a personal computing device 440 or other device operable to store or display user-specific biological indicator data. The output device 410 can also synchronize user-specific biological indicator data with a personal computing device 440 or other device operable to both store and display user-specific biological indicator data. Alternatively, the personal computing device 440 can receive data from a server 430 or cloud-based computing service via the network 420.

The personal computing device 440 can communicate with a server 430 via a network 420, allowing the transfer of user-specific biological indicator data to the server 430. The personal computing device 440 can also communicate user-specific biological indicator data to cloud-based computer services or cloud-based data clusters via the network 420. The personal computing device 440 can also synchronize user-specific biological indicator data with the output device 410 or other device operable to store and/or display user-specific biological indicator data.

The optical-electronic device 400 can also directly communicate data via the network 420 to a server 430 or cloud-based computing and data storage service. In at least one example, the device 400 can include a GPS module operable to communicate with GPS satellites (not shown) to obtain geographic position information.

The optical-electronic device 400 can be used by itself or in combination with other optical-electronic devices or biosensors. For example, the optical-electronic device 400 can be used in combination with heart rate (HR) biosensor devices, foot pod biosensor devices, and/or power meter biosensor devices. The optical-electronic device 400 can also be used in combination with ANT+™ wireless technology and devices that use ANT+™ wireless technology. The optical-electronic device 400 can be used to aggregate data collected by other biosensors including data collected by devices that use ANT+™ technologies. Aggregation of the biosensor data can be via a wireless technology, such as BLUETOOTH®, infrared technology, or radio technology, or can be through a wire.

The biosensor data aggregated by the optical-electronic device 400 can be communicated via a network 420 to a server 430 or to cloud-based computer services or cloud-based data clusters. The aggregated biosensor data can also be communicated from the optical-electronic device 400 to the output device 410 or personal computing device 440.

In at least one example, the optical-electronic device 400 can employ machine learning algorithms by comparing data collected in real-time with data for the same user previously stored on a server 430, output device 410, or in a cloud-based storage service. The machine learning algorithm can also be performed on or by any one of the output device 410, cloud-based computer service, server 430, or personal computing device 440, or any combination thereof.

What is claimed is:

1. A system operable to generate and process tissue-monitoring signals, comprising:
    at least one optical emitter;
    a processor coupled to the at least one optical emitter and operable to execute instructions to generate a corresponding at least one emitted signal;
    a photodetector operable to detect one or more photons transmitted through tissue from the at least one optical emitter and to convert the detected one or more photons into a detected signal; and
    wherein the processor is operable to execute instructions to demodulate each of the at least one emitted signal and the detected signal by cross-correlating each of the at least one emitted signal and the detected signal;
    wherein each of the at least one emitted signal is at least one broadband signal; wherein the processor is further operable to execute instructions to determine an amplitude of a correlation peak given by the cross-correlation of the at least one emitted signal and the detected signal; wherein the amplitude of the correlation peak is operable to be modified by adjusting a time-bandwidth product of the at least one emitted signal.

2. The system of claim 1, wherein each of the at least one emitted signal is a frequency chirp.

3. The system of claim 1, wherein each of the at least one emitted signal generated by the processor is a maximum length pseudorandom number sequence.

4. The system of claim 1, wherein each of the at least one emitted signal comprises at least two emitted signals that are orthogonal to one another.

5. The system of claim 4, wherein the at least two orthogonal signals are generated by multiplying the emitted signal repeatedly by individual columns of a Hadamard matrix.

6. The system of claim 1, wherein the demodulation of each of the at least one emitted signal and the detected signal is performed for at least one of the following: to separate the detected signal generated by at least one emitted signal, to cancel out noise, to cancel out ambient light, to cancel out motion, to increase a signal-to-noise ratio, and to reduce interference.

7. The system of claim 1, wherein the processor is further operable to use the amplitude of the correlation peak to determine information about an optical transmission of the tissue for a given wavelength and emitter/detection separation.

8. The system of claim 1, wherein the amplitude of the correlation peak is modified to adjust separation of the detected signal generated by at least one emitted signal.

9. The system of claim 1, wherein the amplitude of the correlation peak is modified to cancel out at least one of noise, ambient light, or motion.

10. The system of claim 1, wherein the amplitude of the correlation peak is modified to increase a signal-to-noise ratio.

11. The system of claim 1, wherein the amplitude of the correlation peak is modified to reduce interference.

12. The system of claim 7, wherein the information about the optical transmission of the tissue at a given wavelength is used to determine at least one tissue property.

13. A method for generating and processing tissue-monitoring signals, the method comprising:
providing an optical-electronic device, the optical-electronic device including:
at least one optical emitter;
a processor coupled with the at least one optical emitter;
a photodetector;
generating, by the processor, at least one emitted signal for each of the at least one optical emitter;
receiving each of the at least one emitted signal;
controlling each of the at least one optical emitter to emit the at least one emitted signal;
detecting, at the photodetector, one or more photons transmitted through tissue from each of the at least one optical emitter;
converting, at the photodetector, the detected photons into a detected signal;
demodulating, at the processor, each of the at least one emitted signal and the detected signal by cross-correlating each of the at least one emitted signal and the detected signal;
determining, at the processor, an amplitude of a correlation peak given by the cross-correlation of each of the at least one emitted signal and the detected signal; and
modifying, at the processor, the amplitude of the correlation peak by adjusting a time-bandwidth product of the at least one emitted signal, wherein each of the at least one emitted signal is at least one broadband signal.

14. The method of claim 13, wherein the demodulation of each of the at least one emitted signal and the detected signal comprises: demodulating the detected signal and each of the at least one emitted signal, to cancel out noise, to cancel out ambient light, to cancel out motion, to increase a signal-to-noise ratio, and to reduce interference.

15. The method of claim 13, further comprising:
determining, at the processor, an information about an optical transmission of the tissue at a given wavelength by using the amplitude of the correlation peak given by the cross-correlation of each of the at least one emitted signal and the detected signal.

16. The method of claim 13, wherein each of the at least one emitted signal comprises two emitted signals that are orthogonal to one another.

17. The method of claim 16, wherein the two orthogonal emitted signals are generated by multiplying the emitted signal by rows of a Hadamard matrix.

18. The method of claim 16, wherein the two orthogonal signals are generated by using segments of a maximum length binary sequence.

19. The method of claim 16, wherein the two orthogonal signals are generated by using sine waves of different frequencies.

* * * * *